US009212350B2

(12) United States Patent
Bhardwaj et al.

(10) Patent No.: US 9,212,350 B2
(45) Date of Patent: Dec. 15, 2015

(54) METHOD OF CLONING STABLE STRESS TOLERANT SUPEROXIDE DISMUTASE USING UNIVERSAL PRIMERS

(75) Inventors: Pardeep Kumar Bhardwaj, Palampur (IN); Arun Kumar, Palampur (IN); Amit Kishore, Palampur (IN); Sanjay Ghawana, Palampur (IN); Arti Rani, Palampur (IN); Kashmir Singh, Palampur (IN); Harsharan Singh, Palampur (IN); Ravi Shankar Singh, Palampur (IN); Hitesh Kumar, Palampur (IN); Payal Sood, Palampur (IN); Som Dutt, Palampur (IN); Sanjay Kumar, Palampur (IN); Paramvir Singh Ahuja, Palampur (IN)

(73) Assignee: Council of Scientific and Industrial Research, New Delhi (IN)

( * ) Notice: Subject to any disclaimer, the term of this patent is extended or adjusted under 35 U.S.C. 154(b) by 1313 days.

(21) Appl. No.: 12/935,881

(22) PCT Filed: Mar. 31, 2009

(86) PCT No.: PCT/IN2009/000211
§ 371 (c)(1),
(2), (4) Date: Oct. 31, 2011

(87) PCT Pub. No.: WO2009/122441
PCT Pub. Date: Oct. 8, 2009

(65) Prior Publication Data
US 2012/0070835 A1  Mar. 22, 2012

(30) Foreign Application Priority Data

Mar. 31, 2008 (IN) .............................. 846/DEL/2008

(51) Int. Cl.
*C12P 19/34* (2006.01)
*C07H 21/04* (2006.01)
*C12N 9/02* (2006.01)
*C12N 15/82* (2006.01)
*C12Q 1/68* (2006.01)

(52) U.S. Cl.
CPC .......... *C12N 9/0089* (2013.01); *C12N 15/8271* (2013.01); *C12Q 1/6895* (2013.01)

(58) Field of Classification Search
USPC .............................. 435/6.12, 91.2; 536/24.33
See application file for complete search history.

(56) References Cited

U.S. PATENT DOCUMENTS

| | | | |
|---|---|---|---|
| 5,962,271 A | 10/1999 | Chenchik et al. | 435/91.1 |
| 5,962,272 A | 10/1999 | Chenchik et al. | 435/91.1 |
| 6,485,950 B1 | 11/2002 | Kumar et al. | 435/189 |
| 6,869,773 B2 * | 3/2005 | Hoshino et al. | 435/67 |
| 7,037,697 B2 | 5/2006 | Kumar et al. | 435/189 |
| 2010/0261268 A1 | 10/2010 | Bhardwaj et al. | 435/320.1 |

FOREIGN PATENT DOCUMENTS

WO  WO 2007/113615  10/2007

OTHER PUBLICATIONS

Ruiz-Lozano et al., J. Exp. Botany 52(364), 2241-2242 (2001).*
Banks et al., "A second superoxide dismutase gene in the medfly, Ceratitis capitata," *Genetics*, 140:697-702, 1995.
Database EMBL [Online] May 8, 2007, "Carragana jubatra copper/zinc superoxide dismutase mRNA, complete cds," retrieved from EBI accession No. EMBL:EF530044. DP002549871.
Database EMBL [Online] Sep. 4, 2004. "Camellia sinessis Cu/Zn superoxide dismutase mRNA, partial cds," retrieved from EBI accession No. EMBL:AY694187. XP002549870.
Frohman et al., "Rapid production of full-length cDNAs from rare transcripts: amplification using a single gene-specific oligonucleotide primer," *Proc. Natl. Acad. Sci.*, 85:8998-9002, 1988.
Hernandez-Saavedra et al., "Cloning and sequencing of a cDNA encoding a copper-zinc superoxide dismutase enzyme from the marine yeast Debaryomyces hansenii," *Yeast*, 14:573-581, 1998.
Lin et al., "Copper/zinc-superoxide dismutase from lemon cDNA and enzyme stability," *Journal of Agricultural and Food Chemistry*, 50(25):7264-7270, 2002.
Linhart et al., "The degenerate primer design problem: Theory and applications," *Journal of Computational Biology*, 12(4):431-456, 2005.
Liu et al., "The Electronic Plant Gene Register," *Plant Physiol*, 116:867-9, 1998.
PCT International Preliminary Report on Patentability issued in International application No. PCT/IN2009/000211, dated Sep. 8, 2010.
PCT International Search Report and Written Opinion issued in International application No. PCT/IN2009/000211, dated Oct. 29, 2009.
Plantivaux et al, "Molecular characterization of two CuZn-superoxide dismutases in a sea anemone," *Free Radical Biology and Medicine*, 27:1170-1181, 2004.
Sakamoto et al., "Nucleotide sequence of cDNA for the cytosolic Cu/Zn-superoxide dismutase from spinach (*Spinacia oleracea* L.)" *Nucleic Acids Research*, 18:4923, 1990.
Sambrook et al., Molecular Cloning: A Laboratory Manual, Cold Spring Harbor Press, Plainview, NY, 1989.
Singh et al., "Differential expression of Histone H3 gene in tea (*Camellia sinesis* (L.) O. Kuntze) suggests its role in growing tissue," Molecular Biology Reports, 36(3):537-542, 2008.

* cited by examiner

*Primary Examiner* — Kenneth Horlick
(74) *Attorney, Agent, or Firm* — Norton Rose Fulbright US LLP

(57) ABSTRACT

The present invention relates to a method of cloning stable stress tolerant superoxide dismutase from diverse plant species using universal primers.

29 Claims, 7 Drawing Sheets

Figure 1:
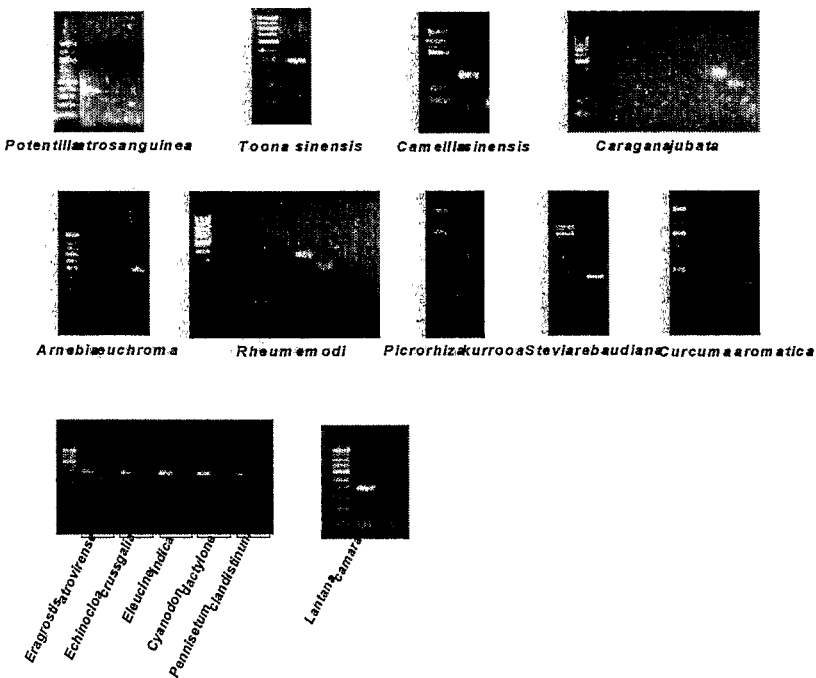

SEQUENCE LISTING

```
<160> NUMBER OF SEQ ID NOS: 79

<210> SEQ ID NO 1
<211> LENGTH: 387
<212> TYPE: DNA
<213> ORGANISM: Potentilla atrosanguinea

<400> SEQUENCE: 1
caagagggag atggcccaac tactgtgacc ggaaacattt ctggcctcaa gcctgggctt        60
catggtttcc atgttcatgc tcttggggac acaaccaatg gttgcatgtc aactggacca       120
catttcaatc ctgctggcaa agagcatggg tctcctgaag atgagactcg tcatgctggt       180
gatcttggaa atatcactgt tggggatgac ggaactgctt gcttcacaat tgttgacaaa       240
cagattcctc tcactggacc acactctatc attggtaggg ctgttgttgt ccatgcagat       300
cctgatgacc ttggcaaggg tggacatgag cttagcaaat ccactggaaa tgctggtggc       360
aggatagctt gtggtattat tggcctt                                           387

<210> SEQ ID NO 2
<211> LENGTH: 279
<212> TYPE: DNA
<213> ORGANISM: Potentilla atrosanguinea

<400> SEQUENCE: 2
tcaactggac cacatttcaa tcctgctggc aaagagcatg ggtctcctga agatgagact        60
cgtcatgctg gtgatcttgg aaatatcact gttggggatg acggaactgc ttgcttcaca       120
attgttgaca aacagattcc tctcactgga ccacactcta tcattggtag ggctgttgtt       180
gtccatgcag atcctgatga ccttggcaag ggtggacatg agcttagcaa atccactgga       240
aatgctggtg gcaggatagc ttgtggtatt attggcctt                              279

<210> SEQ ID NO 3
<211> LENGTH: 387
<212> TYPE: DNA
<213> ORGANISM: Camellia sinensis

<400> SEQUENCE: 3
caggaaggag atggtccaac cactgtgact ggaaacattt ctggcctcaa gcctgggctt        60
catggtttcc atgttcatgc tcttggggac acaaccaatg gttgcatgtc aactggacca       120
catttcaatc ctgctggcaa agagcatggg tctcctgaag atgagactcg tcatgctggt       180
gatcttggaa atatcactgt tggggatgac ggaactgctt gcttcacaat tgttgacaaa       240
```

| | |
|---|---:|
| cagattcctc tcactggacc acactctatc attggtaggg ccgttgttgt ccatgcagac | 300 |
| cctgatgacc ttggcaaggg tggacatgag cttagcaaat ccactggcaa tgctggtggc | 360 |
| aggatagctt gtggtattgg acttcaa | 387 |

<210> SEQ ID NO 4
<211> LENGTH: 390
<212> TYPE: DNA
<213> ORGANISM: Caragana jubata

<400> SEQUENCE: 4

| | |
|---|---:|
| caggagggaa atggcccaac cactgtaact ggaaatcttg ctggtcttaa gcctggcctc | 60 |
| catggcttcc atgttcatgc tttgggggac accacaaatg gttgtctgtc aactggacca | 120 |
| catttcaatc ctcaaggcaa agaacatggt gcccccgagg atgtgaatcg tcatgctggt | 180 |
| gatctaggaa atgttaatgt cggtgatgat ggaaccgcaa aattcactat taccgacagt | 240 |
| cagatcccac tcactggtcc aaactccatc ataggaaggg ctgttgttgt ccatggtgat | 300 |
| cctgatgatc ttgggaaagg tgggcatgaa cttagcaaaa ctaccggaaa tgctggtggc | 360 |
| agagtagctt gtggcattat tggtctgcag | 390 |

<210> SEQ ID NO 5
<211> LENGTH: 390
<212> TYPE: DNA
<213> ORGANISM: Arnebia euchroma

<400> SEQUENCE: 5

| | |
|---|---:|
| caagagggag atggcccaac tactgtgacc ggaaacattt ctggcctcaa gcctgggctt | 60 |
| catggtttcc atgttcatgc tcttggggac acaaccaatg gttgcatgtc aactggacca | 120 |
| catttcaatc ctgctggcaa agagcatggg tctcctgaag atgagactcg tcatgctggt | 180 |
| gatcttggca acatcactgt tggagaagat gggactgctt ctttcaccat tgttgacaag | 240 |
| cagcttccac ttactggact aacttctatc attggaagag ctgtagttgt gcatgctgat | 300 |
| cctgatgatt tgggaaaggg tggccacgag ctcagcaaaa gcacaggaaa tgctggagga | 360 |
| aggattgctt gtggtattat tgggttacag | 390 |

<210> SEQ ID NO 6
<211> LENGTH: 390
<212> TYPE: DNA
<213> ORGANISM: Rheum emodi

<400> SEQUENCE: 6

| | |
|---|---:|
| caagacggag agggcccaac aactgttaca ggaactgtgt ctggccttaa gccaggcctt | 60 |
| catggattcc atgtgcacgc tcttggtgac acaacaaatg gctgcatgtc aactggacca | 120 |
| catttcaatc ctaatgcgaa agagcatggt gcaccggagg atgaaaatcg tcatgcaggt | 180 |
| gatcttggga atattactgc tggcgccgat ggtactgcag ctgtcaatgt tgtagacagt | 240 |
| cagattcctc ttgttggacc aaactcaatc attggaaggg cggtggttgt tcatgctgat | 300 |
| ccggatgacc ttggcaaggg tggtcatgaa ctgagcacga ccacaggaaa tgctggagga | 360 |
| agaattgctt gtggtatcat tggattgcag | 390 |

<210> SEQ ID NO 7
<211> LENGTH: 396
<212> TYPE: DNA
<213> ORGANISM: Picrorhiza kurrooa

<400> SEQUENCE: 7

```
caggaaggag atggcccaac cactgtaact ggaaatcttg ctggtcttaa gcctggcctc    60
catggcttcc atgttcatgc tttgggggac accacaaatg gttgtctgtc aactggacca   120
catttcaatc ctcaaggcaa agaaacatgg tgccccgag gatgagaaat cgtcatgctg    180
gtgatcttag gaaaatgtta atgtcgggtg atgatgaaa ccgccaaaat tcacttatta   240
ccgacagtca gaatcccact tcactgggtc caaactccat cataggaaag gggctgttgg   300
ttggtccaat gggtgatccc tgatgatctt tggggaaagg gtggggccat gcaactttag   360
ccaaaactta cccgggaaaa tgcccgggtg ggccag                             396

<210> SEQ ID NO 8
<211> LENGTH: 361
<212> TYPE: DNA
<213> ORGANISM: Stevia rebaudiana

<400> SEQUENCE: 8
caggaaggag atggtccaac aactgtgaat gtcaaaataa ctggattaac tccaggaccc    60
catgggtttc atcttcatga gtttggtgat accacaaatg ggtgcatatc aacaggacca   120
cattttaacc caaatgggca tacacacggt gctcctgaag atgaaatccg ccacgcgggc   180
gacctgggaa acataattgc caacgccgat ggcgtggctg aggctacaat tgttgataac   240
cagataccat tgagcgggcc taatgctgtg gttggaagag catttgtggt tcatgagctc   300
gctgatgatc ttggaaaggg tggtcacgaa cttagctctc aactgaataa gcaggtccac   360
c                                                                    361

<210> SEQ ID NO 9
<211> LENGTH: 390
<212> TYPE: DNA
<213> ORGANISM: Curcuma aromatica

<400> SEQUENCE: 9
caggaaggag atggtccaac caccgtcact ggatccatca ctggcctcaa ggctgggctt    60
catggcttcc atgtgcatgc tcttggagac accaccaatg gatgcatgtc aactgggcct   120
cattttaatc ctgctggaaa ggaacatggt gctcctgaag atgtaaaccg acatgctggt   180
gatctaggca atgtcactgc tagcgaggat ggtattgttg ctgtctctgt tgttgacaaa   240
cagatccctc tcactggacc acactctatc attggtaggg ctgttgttgt ccatgcagat   300
cctgatgacc ttggcaaggg tggacatgag cttagcaaat ccactggaaa tgctggtggc   360
aggatagctt gtggtattat tggccttcaa                                     390

<210> SEQ ID NO 10
<211> LENGTH: 386
<212> TYPE: DNA
<213> ORGANISM: Eragrostis atrovirens

<400> SEQUENCE: 10
caggaaggag atggtccaac cactgtaact ggaaatcttt ctggtcttaa gcctggcctc    60
catggattcc atatccatgc tttgggggac accacaaatg gttgcttgtc aactggacca   120
catttcaatc ctaatgggaa ggatcatggt gcccctgagg atgagactcg acatgctggt   180
gatttaggaa atattaatgt tggtgatgat ggaactgtaa gcttcactat tactgactat   240
cagatccctc tcactggacc aaactctatc ataggaaggg ctgttgttgt tcatgctgat   300
cctgatgatc ttggggaaagg tggtcatgag cttagcaaaa ctactggaaa tgctggtggc   360
```
agaatagctt gtggcatcgg tcttca    386

<210> SEQ ID NO 11
<211> LENGTH: 387
<212> TYPE: DNA
<213> ORGANISM: Echinocloa crussaglli

<400> SEQUENCE: 11
caggaaggag atggcccaac cactgtgact ggaagtgtct ctgggcttaa gccggggctc    60
catgggttcc atgtgcatgc gcttggtgac accaccaatg gctgcatgtc gactgggcca    120
cacttcaatc ctgctggtaa ggagcatggt gcaccggaag atgagaaccg ccatgccggt    180
gatcttggga atgtgacagc tggagaagat ggtgttgcta atgtcaatat tactgatagt    240
cagatccctc tcactgggcc gcactcgatc attggccgag ctgtagttgt ccatgctgat    300
cctgatgacc ttgcaagggg tggacatgag ctgagcaaga gcactggaaa tgctggcggc    360
cgtgttgctt gtggcatcgg acttcag    387

<210> SEQ ID NO 12
<211> LENGTH: 386
<212> TYPE: DNA
<213> ORGANISM: Eleucine indica

<400> SEQUENCE: 12
caggaaggag atggtccaac aactgtaact ggaagcccttt ccggcctcaa gcctggtctt    60
catggattcc atgttcacgc ccttggggac acaacaaatg gttgcatgtc gactggagcg    120
cattataatc ctgctggcaa agaacatggt gccccagagg atgagaatcg ccatgctggt    180
gatctaggaa atgtcaatgt tggtgatgat ggtactgtta attttacaat tgttgacagt    240
cagattcctc ttgttggacc aaattccatt attggaaggg ctgctgtggt ccacgcagat    300
cccgatgatc ttgcaagggg tgggcatgag ctcagcaaaa ccactggaaa tgctggtggc    360
agactagctt gtggtatcgg gcttca    386

<210> SEQ ID NO 13
<211> LENGTH: 386
<212> TYPE: DNA
<213> ORGANISM: Cynodon dactylon

<400> SEQUENCE: 13
caggaaggag atggtccaac aacagtcaat gttcgaatca ctggccttac cccagggctt    60
catggttttc acctgcatga gtatggtgat accacaaatg ggtgtatctc aacaggacca    120
cattttaacc ctaaccagtt gacacatggt gctcctgaag atgaaatccg tcatgcgggt    180
gacctgggaa acgtagttgc tgatgccaat ggggttgcag aggcaacaat cgtgacaat    240
cagataccac tcactggccc caattcagtt gttgggagag ccttagtggt tcacgagctt    300
gaagatgacc tcggaaaggg tggacatgaa cttagtttga gcactggaaa tgctggtgga    360
agattagctt gtggcatcgg acttca    386

<210> SEQ ID NO 14
<211> LENGTH: 387
<212> TYPE: DNA
<213> ORGANISM: Pennisetum clandistinum

<400> SEQUENCE: 14
caggaaggag atggcccaac cactgtaact ggaaatcttt ctggtcttaa gcctggcctc    60
catggattcc atatccatgc tttgggggac accacaaatg gttgcttgtc aactggacca    120

```
catttcaatc ctaatgggaa ggatcatggt gcccctgagg atgagactcg acatgctggt    180
gatttaggaa atattaatgt tggtgatgat ggaactgtaa gcttcactat tactgactat    240
cagatccctc tcactggacc aaactctatc ataggaaggg ctgttgttgt tcatgctggt    300
cctgatgatc ttgggaaagg tggtcatgag cttagcaaaa ctactggaaa tgctggtggc    360
agaatagctt gtggcattgg gcttcaa                                        387
```

<210> SEQ ID NO 15
<211> LENGTH: 386
<212> TYPE: DNA
<213> ORGANISM: Toona sinensis

<400> SEQUENCE: 15

```
caggaaggag atggcccaac cactgtaact ggaaatcttt ctggtcttaa gcctggcctc     60
catggattcc atatccatgc tttgggggac accacaaatg gttgcttgtc aactggacca    120
catttcaatc ctaatgggaa ggatcatggt gcccctgagg atgagactcg acatgctggt    180
gatttaggaa atattaatgt tggtgatgat ggaactgtaa gcttcactat tactgactat    240
cagatccctc tcactggacc aaactctatc ataggaaggg ctgttgttgt tcatgctgat    300
cctgatgatc ttgggaaagg tggtcatgag cttagcaaaa ctactggaaa tgctggtggc    360
agaatagctt gtggcattgg acttca                                         386
```

<210> SEQ ID NO 16
<211> LENGTH: 390
<212> TYPE: DNA
<213> ORGANISM: Lantana camara

<400> SEQUENCE: 16

```
caggaaggag atgatactac aactgttacc ggaagtcttt ctggcctgaa gcctggacaa     60
cacggctttc acgtacacgc acttggtgac accaccaacg gttgcatgtc aactgggcct    120
cacttcaacc ctggtggcaa agagcatggc gctcctgggg atgagaatcg ccatgctggt    180
gaccttggaa atgtcacagt tggtgaagat ggcaaagctt ctttcaccgt cgttgataag    240
cagattccac ttactggacc acactccatc atcggaagag ctgtagttgt tcacgctgat    300
cccgatgatc ttggaaaggg tggacacgag ttgagcaaaa ccactggaaa tgctggtgga    360
agagttgctt gcggcatcat tggtcttcag                                     390
```

<210> SEQ ID NO 17
<211> LENGTH: 129
<212> TYPE: PRT
<213> ORGANISM: Potentilla atrosanguinea

<400> SEQUENCE: 17

```
Gln Glu Gly Asp Gly Pro Thr Thr Val Thr Gly Asn Ile Ser Gly Leu
1               5                   10                  15

Lys Pro Gly Leu His Gly Phe His Val His Ala Leu Gly Asp Thr Thr
            20                  25                  30

Asn Gly Cys Met Ser Thr Gly Pro His Phe Asn Pro Ala Gly Lys Glu
        35                  40                  45

His Gly Ser Pro Glu Asp Glu Thr Arg His Ala Gly Asp Leu Gly Asn
    50                  55                  60

Ile Thr Val Gly Asp Asp Gly Thr Ala Cys Phe Thr Ile Val Asp Lys
65                  70                  75                  80

Gln Ile Pro Leu Thr Gly Pro His Ser Ile Ile Gly Arg Ala Val Val
```

```
                        85                  90                  95

Val His Ala Asp Pro Asp Leu Gly Lys Gly Gly His Glu Leu Ser
                100                 105                 110

Lys Ser Thr Gly Asn Ala Gly Gly Arg Ile Ala Cys Gly Ile Gly
            115                 120                 125

Leu

<210> SEQ ID NO 18
<211> LENGTH: 129
<212> TYPE: PRT
<213> ORGANISM: Curcuma aromatica

<400> SEQUENCE: 18

Gln Glu Gly Asp Gly Pro Thr Thr Val Thr Gly Asn Ile Ser Gly Leu
1               5                   10                  15

Lys Pro Gly Leu His Gly Phe His Val His Ala Leu Gly Asp Thr Thr
            20                  25                  30

Asn Gly Cys Met Ser Thr Gly Pro His Phe Asn Pro Ala Gly Lys Glu
        35                  40                  45

His Gly Ser Pro Glu Asp Glu Thr Arg His Ala Gly Asp Leu Gly Asn
    50                  55                  60

Ile Thr Val Gly Asp Asp Gly Thr Ala Cys Phe Thr Ile Val Asp Lys
65                  70                  75                  80

Gln Ile Pro Leu Thr Gly Pro His Ser Ile Ile Gly Arg Ala Val Val
                85                  90                  95

Val His Ala Asp Pro Asp Leu Gly Lys Gly Gly His Glu Leu Ser
                100                 105                 110

Lys Ser Thr Gly Asn Ala Gly Gly Arg Ile Ala Cys Gly Ile Gly Leu
            115                 120                 125

Gln

<210> SEQ ID NO 19
<211> LENGTH: 130
<212> TYPE: PRT
<213> ORGANISM: Lantana camara

<400> SEQUENCE: 19

Gln Glu Gly Asp Asp Thr Thr Thr Val Thr Gly Ser Leu Ser Gly Leu
1               5                   10                  15

Lys Pro Gly Gln His Gly Phe His Val His Ala Leu Gly Asp Thr Thr
            20                  25                  30

Asn Gly Cys Met Ser Thr Gly Pro His Phe Asn Pro Gly Gly Lys Glu
        35                  40                  45

His Gly Ala Pro Gly Asp Glu Asn Arg His Ala Gly Asp Leu Gly Asn
    50                  55                  60

Val Thr Val Gly Glu Asp Gly Lys Ala Ser Phe Thr Val Val Asp Lys
65                  70                  75                  80

Gln Ile Pro Leu Thr Gly Pro His Ser Ile Ile Gly Arg Ala Val Val
                85                  90                  95

Val His Ala Asp Pro Asp Leu Gly Lys Gly Gly His Glu Leu Ser
                100                 105                 110

Lys Thr Thr Gly Asn Ala Gly Gly Arg Val Ala Cys Gly Ile Ile Gly
            115                 120                 125

Leu Gln
    130
```

<210> SEQ ID NO 20
<211> LENGTH: 459
<212> TYPE: DNA
<213> ORGANISM: Curcuma aromatica

<400> SEQUENCE: 20

| | | | | | |
|---|---|---|---|---|---|
| atggtgaagg | ctgttgctgt | cctgggtagc | agtgagggtg | ttaagggcac | aatttacttc | 60 |
| gtccaggaag | gagatggtcc | aaccaccgtc | actggatcca | tcactggcct | caaggctggg | 120 |
| cttcatggct | tccatgtgca | tgctcttgga | gacaccacca | atggatgcat | gtcaactggg | 180 |
| cctcatttta | atcctgctgg | aaaggaacat | ggtgctcctg | aagatgtaaa | ccgacatgct | 240 |
| ggtgatctag | gcaatgtcac | tgctagcgag | gatggtattg | ttgctgtctc | tgttgttgac | 300 |
| aaacagatcc | ctctcactgg | accacactct | atcattggta | gggctgttgt | tgtccatgca | 360 |
| gatcctgatg | accttggcaa | gggtggacat | gagcttagca | aatccactgg | aaatgctggt | 420 |
| ggcaggatag | cttgtggtat | tattggcctt | caaggatga | | | 459 |

<210> SEQ ID NO 21
<211> LENGTH: 152
<212> TYPE: PRT
<213> ORGANISM: Curcuma aromatica

<400> SEQUENCE: 21

Met Val Lys Ala Val Ala Val Leu Gly Ser Ser Glu Gly Val Lys Gly
1               5                   10                  15

Thr Ile Tyr Phe Val Gln Glu Gly Asp Gly Pro Thr Thr Val Thr Gly
            20                  25                  30

Ser Ile Thr Gly Leu Lys Ala Gly Leu His Gly Phe His Val His Ala
        35                  40                  45

Leu Gly Asp Thr Thr Asn Gly Cys Met Ser Thr Gly Pro His Phe Asn
    50                  55                  60

Pro Ala Gly Lys Glu His Gly Ala Pro Glu Asp Val Asn Arg His Ala
65                  70                  75                  80

Gly Asp Leu Gly Asn Val Thr Ala Ser Glu Asp Gly Ile Val Ala Val
                85                  90                  95

Ser Val Val Asp Lys Gln Ile Pro Leu Thr Gly Pro His Ser Ile Ile
            100                 105                 110

Gly Arg Ala Val Val Val His Ala Asp Pro Asp Leu Gly Lys Gly
        115                 120                 125

Gly His Glu Leu Ser Lys Ser Thr Gly Asn Ala Gly Gly Arg Ile Ala
    130                 135                 140

Cys Gly Ile Ile Gly Leu Gln Gly
145                 150

<210> SEQ ID NO 22
<211> LENGTH: 459
<212> TYPE: DNA
<213> ORGANISM: Caragana jubata

<400> SEQUENCE: 22

| | | | | | |
|---|---|---|---|---|---|
| atggtgaagg | ctgtggcagt | tcttggcagc | aatgagggtg | tcactggaac | tatttccttc | 60 |
| agtcaggagg | gaaatggccc | aaccactgta | actggaaatc | ttgctggtct | taagcctggc | 120 |
| ctccatggct | tccatgttca | tgctttgggg | gacaccacaa | atggttgtct | gtcaactgga | 180 |
| ccacatttca | atcctcaagg | caaagaacat | ggtgcccccg | aggatgtgaa | tcgtcatgct | 240 |
| ggtgatctag | gaaatgttaa | tgtcggtgat | gatggaaccg | caaaattcac | tattaccgac | 300 |

```
agtcagatcc cactcactgg tccaaactcc atcataggaa gggctgttgt tgtccatggt    360
gatcctgatg atcttgggaa aggtgggcat gaacttagca aaactaccgg aaatgctggt    420
ggcagagtag cttgtggcat tattggtctg cagggataa                          459
```

<210> SEQ ID NO 23
<211> LENGTH: 152
<212> TYPE: PRT
<213> ORGANISM: Caragana jubata

<400> SEQUENCE: 23

```
Met Val Lys Ala Val Ala Val Leu Gly Ser Asn Glu Gly Val Thr Gly
1               5                   10                  15

Thr Ile Ser Phe Ser Gln Glu Gly Asn Gly Pro Thr Thr Val Thr Gly
            20                  25                  30

Asn Leu Ala Gly Leu Lys Pro Gly Leu His Gly Phe His Val His Ala
        35                  40                  45

Leu Gly Asp Thr Thr Asn Gly Cys Leu Ser Thr Gly Pro His Phe Asn
    50                  55                  60

Pro Gln Gly Lys Glu His Gly Ala Pro Glu Asp Val Asn Arg His Ala
65                  70                  75                  80

Gly Asp Leu Gly Asn Val Asn Val Gly Asp Asp Gly Thr Ala Lys Phe
                85                  90                  95

Thr Ile Thr Asp Ser Gln Ile Pro Leu Thr Gly Pro Asn Ser Ile Ile
            100                 105                 110

Gly Arg Ala Val Val Val His Gly Asp Pro Asp Asp Leu Gly Lys Gly
        115                 120                 125

Gly His Glu Leu Ser Lys Thr Thr Gly Asn Ala Gly Gly Arg Val Ala
    130                 135                 140

Cys Gly Ile Ile Gly Leu Gln Gly
145                 150
```

<210> SEQ ID NO 24
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 24

```
caggaaggag atggnccaac n                                              21
```

<210> SEQ ID NO 25
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n = c or t
<220> FEATURE:
<221> NAME/KEY: misc_feature
<222> LOCATION: (6)..(7)

```
<223> OTHER INFORMATION: n = a or g
<220> FEATURE:
<221> NAME/KEY: misc_feature
<222> LOCATION: (10)..(10)
<223> OTHER INFORMATION: n = a or g
<220> FEATURE:
<221> NAME/KEY: misc_feature
<222> LOCATION: (13)..(13)
<223> OTHER INFORMATION: n = a, c or g

<400> SEQUENCE: 25
ntgaannccn atnccacaag c                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n = a or t
<220> FEATURE:
<221> NAME/KEY: misc_feature
<222> LOCATION: (6)..(6)
<223> OTHER INFORMATION: n = c or t
<220> FEATURE:
<221> NAME/KEY: misc_feature
<222> LOCATION: (9)..(9)
<223> OTHER INFORMATION: n = a, g or t
<220> FEATURE:
<221> NAME/KEY: misc_feature
<222> LOCATION: (12)..(12)
<223> OTHER INFORMATION: n = a or g
<220> FEATURE:
<221> NAME/KEY: misc_feature
<222> LOCATION: (15)..(15)
<223> OTHER INFORMATION: n = c or t
<220> FEATURE:
<221> NAME/KEY: misc_feature
<222> LOCATION: (18)..(18)
<223> OTHER INFORMATION: n = c or t

<400> SEQUENCE: 26
tcnacnggnc ncantanaa t                                               21

<210> SEQ ID NO 27
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n = c or t
<220> FEATURE:
<221> NAME/KEY: misc_feature
<222> LOCATION: (6)..(7)
<223> OTHER INFORMATION: n = a or g
<220> FEATURE:
<221> NAME/KEY: misc_feature
<222> LOCATION: (10)..(10)
<223> OTHER INFORMATION: n = a or g
<220> FEATURE:
<221> NAME/KEY: misc_feature
<222> LOCATION: (13)..(13)
<223> OTHER INFORMATION: n = a, g or c

<400> SEQUENCE: 27
ntgaannccn atnccacaag c                                              21
```

```
<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
gttgtaaaac gacggccagt                                                  20

<210> SEQ ID NO 29
<211> LENGTH: 21
<212> TYPE: DNA
<213> ORGANISM: Artificial Sequence
<220> FEATURE:
<223> OTHER INFORMATION: Synthetic primer

<400> SEQUENCE: 29
cacaggaaac agctatgagc c                                                21

<210> SEQ ID NO 30
<211> LENGTH: 18
<212> TYPE: DNA
<213> ORGANISM: Artificial Sequence
<220> FEATURE:
<223> OTHER INFORMATION: Synthetic primer

<400> SEQUENCE: 30
caggaaacag ctatgacc                                                    18

<210> SEQ ID NO 31
<211> LENGTH: 30
<212> TYPE: DNA
<213> ORGANISM: Artificial Sequence
<220> FEATURE:
<223> OTHER INFORMATION: Synthetic primer

<400> SEQUENCE: 31
aagcagtggt atcaacgcag agtacgcggg                                       30

<210> SEQ ID NO 32
<211> LENGTH: 55
<212> TYPE: DNA
<213> ORGANISM: Artificial Sequence
<220> FEATURE:
<223> OTHER INFORMATION: Synthetic primer

<400> SEQUENCE: 32
aagcagtggt atcaacgcag agtacttttt tttttttttt tttttttttt ttttt           55

<210> SEQ ID NO 33
<211> LENGTH: 25
<212> TYPE: DNA
<213> ORGANISM: Artificial Sequence
<220> FEATURE:
<223> OTHER INFORMATION: Synthetic primer

<400> SEQUENCE: 33
tttttttttt tttttttttt ttttt                                            25

<210> SEQ ID NO 34
<211> LENGTH: 44
<212> TYPE: DNA
<213> ORGANISM: Artificial Sequence
<220> FEATURE:
<223> OTHER INFORMATION: Synthetic primer
```

<400> SEQUENCE: 34
taatacgact cactataggg caagcagtgg tatcaacgca gagt         44

<210> SEQ ID NO 35
<211> LENGTH: 22
<212> TYPE: DNA
<213> ORGANISM: Artificial Sequence
<220> FEATURE:
<223> OTHER INFORMATION: Synthetic primer

<400> SEQUENCE: 35
ctaatacgac tcactatagg gc         22

<210> SEQ ID NO 36
<211> LENGTH: 23
<212> TYPE: DNA
<213> ORGANISM: Artificial Sequence
<220> FEATURE:
<223> OTHER INFORMATION: Synthetic primer

<400> SEQUENCE: 36
aagcagtggt atcaacgcag agt         23

<210> SEQ ID NO 37
<211> LENGTH: 27
<212> TYPE: DNA
<213> ORGANISM: Artificial Sequence
<220> FEATURE:
<223> OTHER INFORMATION: Synthetic primer

<400> SEQUENCE: 37
tgggcatgaa cttagcaaaa ctaccgg         27

<210> SEQ ID NO 38
<211> LENGTH: 27
<212> TYPE: DNA
<213> ORGANISM: Artificial Sequence
<220> FEATURE:
<223> OTHER INFORMATION: Synthetic primer

<400> SEQUENCE: 38
gttgttgtcc atggtgatcc tgatgat         27

<210> SEQ ID NO 39
<211> LENGTH: 28
<212> TYPE: DNA
<213> ORGANISM: Artificial Sequence
<220> FEATURE:
<223> OTHER INFORMATION: Synthetic primer

<400> SEQUENCE: 39
tatcactgtt ggggatgacg gaactgct         28

<210> SEQ ID NO 40
<211> LENGTH: 28
<212> TYPE: DNA
<213> ORGANISM: Artificial Sequence
<220> FEATURE:
<223> OTHER INFORMATION: Synthetic primer

<400> SEQUENCE: 40
attggtaggg ctgttgttgt ccatgcag         28

<210> SEQ ID NO 41
<211> LENGTH: 28

```
<212> TYPE: DNA
<213> ORGANISM: Artificial Sequence
<220> FEATURE:
<223> OTHER INFORMATION: Synthetic primer

<400> SEQUENCE: 41
ctgcatggac aacaacagcc ctaccaat                                          28

<210> SEQ ID NO 42
<211> LENGTH: 27
<212> TYPE: DNA
<213> ORGANISM: Artificial Sequence
<220> FEATURE:
<223> OTHER INFORMATION: Synthetic primer

<400> SEQUENCE: 42
gctagcgagg atggtattgt tgctgtc                                           27

<210> SEQ ID NO 43
<211> LENGTH: 28
<212> TYPE: DNA
<213> ORGANISM: Artificial Sequence
<220> FEATURE:
<223> OTHER INFORMATION: Synthetic primer

<400> SEQUENCE: 43
tatcactgtt ggggatgacg gaactgct                                          28

<210> SEQ ID NO 44
<211> LENGTH: 28
<212> TYPE: DNA
<213> ORGANISM: Artificial Sequence
<220> FEATURE:
<223> OTHER INFORMATION: Synthetic primer

<400> SEQUENCE: 44
attggtaggg ctgttgttgt ccatgcag                                          28

<210> SEQ ID NO 45
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: x = met or ile

<400> SEQUENCE: 45

Gly Cys Xaa Ser Thr Gly Pro His
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: x = leu or val

<400> SEQUENCE: 46

Asn Ala Gly Gly Arg Xaa Ala Cys
1               5
```

```
<210> SEQ ID NO 47
<211> LENGTH: 6
<212> TYPE: PRT
<213> ORGANISM: Artificial Sequence
<220> FEATURE:
<223> OTHER INFORMATION: Synthetic peptide

<400> SEQUENCE: 47

His Gly Phe His Val Asn
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic peptide

<400> SEQUENCE: 48

Gly Pro His Phe Asn Pro
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic peptide

<400> SEQUENCE: 49

Gly Cys Gly Val Ile Gly
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic peptide

<400> SEQUENCE: 50

Ala Cys Gly Val Ile Gly
1               5

<210> SEQ ID NO 51
<211> LENGTH: 16
<212> TYPE: PRT
<213> ORGANISM: Artificial Sequence
<220> FEATURE:
<223> OTHER INFORMATION: Synthetic peptide

<400> SEQUENCE: 51

Val Ser Gly Val Val Asn Phe Glu Gln Ser Ser Glu Glu Asp Pro Thr
1               5                   10                  15

<210> SEQ ID NO 52
<211> LENGTH: 14
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n = a or g
<220> FEATURE:
<221> NAME/KEY: misc_feature
<222> LOCATION: (9)..(9)
```

```
<223> OTHER INFORMATION: n =  inosine
<220> FEATURE:
<221> NAME/KEY: misc_feature
<222> LOCATION: (12)..(12)
<223> OTHER INFORMATION: n =  inosine

<400> SEQUENCE: 52
atgaangcng tntg                                                          14

<210> SEQ ID NO 53
<211> LENGTH: 12
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n = a or g
<220> FEATURE:
<221> NAME/KEY: misc_feature
<222> LOCATION: (4)..(4)
<223> OTHER INFORMATION: n = a, g or t
<220> FEATURE:
<221> NAME/KEY: misc_feature
<222> LOCATION: (10)..(10)
<223> OTHER INFORMATION: n =  inosine

<400> SEQUENCE: 53
ngtnatgacn gg                                                            12

<210> SEQ ID NO 54
<211> LENGTH: 26
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n = a or g
<220> FEATURE:
<221> NAME/KEY: misc_feature
<222> LOCATION: (6)..(6)
<223> OTHER INFORMATION: n = c or t
<220> FEATURE:
<221> NAME/KEY: misc_feature
<222> LOCATION: (9)..(9)
<223> OTHER INFORMATION: n = a or g
<220> FEATURE:
<221> NAME/KEY: misc_feature
<222> LOCATION: (12)..(12)
<223> OTHER INFORMATION: n = c or t
<220> FEATURE:
<221> NAME/KEY: misc_feature
<222> LOCATION: (15)..(15)
<223> OTHER INFORMATION: n = a or g
<220> FEATURE:
<221> NAME/KEY: misc_feature
<222> LOCATION: (18)..(18)
<223> OTHER INFORMATION: n = a, g or t
<220> FEATURE:
<221> NAME/KEY: misc_feature
<222> LOCATION: (21)..(21)
<223> OTHER INFORMATION: n =  inosine

<400> SEQUENCE: 54
tcntcntcnt tntcntgnat naccat                                             26

<210> SEQ ID NO 55
<211> LENGTH: 20
<212> TYPE: DNA
<213> ORGANISM: Artificial Sequence
```

```
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 55
gcnggnccnc ayttyaaycc                                              20

<210> SEQ ID NO 56
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 56
ccrcangcna rnckngcnc                                               19

<210> SEQ ID NO 57
<211> LENGTH: 10
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 57 cncgrttncc                                                         10

<210> SEQ ID NO 58
<211> LENGTH: 300
<212> TYPE: DNA
<213> ORGANISM: Arabidopsis thaliana

<400> SEQUENCE: 58
```

```
atggcgaaag gagttgcagt tttgaacagc agtgagggtg ttacggggac tatcttttc    60 acccaggaag gcgatggtgt gaccactgtg agtggaacag tttctggcct taagcctggt   120
cttcatggtt tccatgtcca tgctcttggt gacaccacta acggttgcat gtctactggt   180
ccacatttca accccgatgg taaaacacac ggtgccctg aggatgctaa tcgacatgct    240
ggtgatctag aaacatcac tgttggagat gatggaactg ccaccttcac aatcactgat    300
```

<210> SEQ ID NO 59
<211> LENGTH: 300
<212> TYPE: DNA
<213> ORGANISM: Brassica juncea

<400> SEQUENCE: 59

```
atggccaagg gagttgcagt tttgaacagc agtgagggtg ttaaggggac tatcttcttc    60
acccaggaag gagatggtgc cacaactgtg actggaactg tttctggtct taaacctggt   120
ccccatggtt tccatgtcca tgctcttggt gacaccacca acggttgcat gtctaccggt   180
ccacatttca accctgatgg taaaacccac ggtgcaccg aggatgctaa tcgtcatgct    240
ggagatctag aaacatcat tgttggggat gatggaactg ccaccttcac aatcactgac    300
```

<210> SEQ ID NO 60
<211> LENGTH: 300
<212> TYPE: DNA
<213> ORGANISM: Malus domestica

<400> SEQUENCE: 60

```
atggtgaagg gtgttgctgt tctcggctcc agtgagggcg ttaaaggaac catcagcttt    60
gtccaggagg gagatggccc aactactgtg actggaagtg tctctggcct caagcctgga   120
cttcatggtt tccatgtcca tgctcttgga gacacaacaa acggttgcat gtcaactggg   180
ccacacttca atcctgctgg aaaagagcat ggtgcccctg aagatgagct tcgccatgct   240
ggcgatcttg aaacatcac tgctggggac gatggaactg caaccttcac gattgttgac    300
```

<210> SEQ ID NO 61
<211> LENGTH: 300
<212> TYPE: DNA
<213> ORGANISM: Potentilla atrosanguinea

<400> SEQUENCE: 61

```
atggcaaagg gcgttgctgt acttagctcc agtgagggtg ttgctggaac tatcctcttt    60
acccaagagg gagatggccc aactactgtg accggaaaca tttctggcct caagcctggg   120
cttcatggtt tccatgttca tgctcttggg gacacaacca atggttgcat gtcaactgga   180
ccacatttca atcctgctgg caaagagcat gggtctcctg aagatgagac tcgtcatgct   240
ggtgatcttg aaatatcac tgttggggat gacggaactg cttgcttcac aattgttgac    300
```

<210> SEQ ID NO 62
<211> LENGTH: 300
<212> TYPE: DNA
<213> ORGANISM: Pisum

<400> SEQUENCE: 62

```
atggtgaagg ctgtggcagt tcttagtaac agtaacgaag tctcgggtac tattaacttc    60
agtcaggagg gaaatggtcc aaccactgta actggaactc ttgctggtct taagcctggc   120
ctccacggct tccatatcca tgccttggga gacaccacaa acggttgcat ttcaactgga   180
ccacatttca atcctaatgg gaaggaacat ggtgcccctg aggatgagac tagacatgct   240
```

```
ggtgatttag gaaatatcaa tgttggtgat gatggaactg taagcttcac cattactgac    300
```

<210> SEQ ID NO 63
<211> LENGTH: 300
<212> TYPE: DNA
<213> ORGANISM: Zea mays

<400> SEQUENCE: 63

```
atggtgaagg ctgttgctgt gctgggtagc agcgatggtg tcaagggcac catctttttc    60
acccaagagg gagatggccc taccgctgtc actggaagtg tctctggcct caagcctggc   120
ctccatgggt tccatgtaca tgcacttggt gacaccacca atggatgcat gtcaactgga   180
cacgactaca atcctgcgag caaggagcat ggggcaccag aagatgagaa ccgccatgcc   240
ggtgatcttg gaaatgtgac agctggagca gatggtgttg ctaatatcaa tgtcactgac   300
```

<210> SEQ ID NO 64
<211> LENGTH: 159
<212> TYPE: DNA
<213> ORGANISM: Arabidopsis thaliana

<400> SEQUENCE: 64

```
tgccagattc ctcttactgg accaaactct attgttggta gggctgttgt tgtccatgca    60
gaccctgatg acctcggaaa gggaggccat gaactcagcc tggctactgg aaacgcaggc   120
ggccgtgttg cttgcggcat cattggtctc cagggctaa                          159
```

<210> SEQ ID NO 65
<211> LENGTH: 159
<212> TYPE: DNA
<213> ORGANISM: Brassica juncea

<400> SEQUENCE: 65

```
agccagattc ctcttactgg accaaactct attgtaggaa gggctgttgt tgtccatgca    60
gaccgtgatg accttggaaa gggaggccat gaactcagct tgtctactgg aaatgcagga   120
ggccgtgttg cttgtggtat tattggtctt cagggctaa                          159
```

<210> SEQ ID NO 66
<211> LENGTH: 159
<212> TYPE: DNA
<213> ORGANISM: Malus domestica

<400> SEQUENCE: 66

```
aagcagattc ctctcgctgg accacactct atcattggta gggcggttgt tgtccacgca    60
gaccctgatg accttggcaa gggtggacat gagcttagca aatccacagg aaatgctggt   120
ggcagggtgg cttgcggtat tattggtctg caaggatga                          159
```

<210> SEQ ID NO 67
<211> LENGTH: 159
<212> TYPE: DNA
<213> ORGANISM: Potentilla atrosanguinea

<400> SEQUENCE: 67

```
aaacagattc ctctcactgg accacactct atcattggta gggctgttgt tgtccatgca    60
gatcctgatg accttggcaa gggtggacat gagcttagca aatccactgg aaatgctggt   120
ggcaggatag cttgtggtat tattggcctt caaggatga                          159
```

<210> SEQ ID NO 68

<211> LENGTH: 159
<212> TYPE: DNA
<213> ORGANISM: Pisum

<400> SEQUENCE: 68

```
aaccatatcc ctctcactgg aacaaactcc atcataggaa gggctgttgt tgtccatgcc      60
gatcctgatg atcttgggaa aggtggtcac gagcttagca aaactactgg aaatgctggt     120
ggcagagtag cttgtggtat tattgggttg caaggatag                            159
```

<210> SEQ ID NO 69
<211> LENGTH: 159
<212> TYPE: DNA
<213> ORGANISM: Zea mays

<400> SEQUENCE: 69

```
agccagatcc cactgactgg gccaaactca atcattggca gagctgttgt tgttcacgct      60
gatcctgatg atcttggaaa gggtgggcac gagcttagca agagcactgg aaacgcgggt     120
ggccgtgttg cttgtgggat cattggactc cagggctga                            159
```

<210> SEQ ID NO 70
<211> LENGTH: 152
<212> TYPE: PRT
<213> ORGANISM: Arabidopsis thaliana

<400> SEQUENCE: 70

Met Ala Lys Gly Val Ala Val Leu Asn Ser Ser Glu Gly Val Thr Gly
1               5                   10                  15

Thr Ile Phe Phe Thr Gln Glu Gly Asp Gly Val Thr Val Ser Gly
            20                  25                  30

Thr Val Ser Gly Leu Lys Pro Gly Leu His Gly Phe His Val His Ala
        35                  40                  45

Leu Gly Asp Thr Thr Asn Gly Cys Met Ser Thr Gly Pro His Phe Asn
    50                  55                  60

Pro Asp Gly Lys Thr His Gly Ala Pro Glu Asp Ala Asn Arg His Ala
65                  70                  75                  80

Gly Asp Leu Gly Asn Ile Thr Val Gly Asp Gly Thr Ala Thr Phe
            85                  90                  95

Thr Ile Thr Asp Cys Gln Ile Pro Leu Thr Gly Pro Asn Ser Ile Val
            100                 105                 110

Gly Arg Ala Val Val Val His Ala Asp Pro Asp Asp Leu Gly Lys Gly
        115                 120                 125

Gly His Glu Leu Ser Leu Ala Thr Gly Asn Ala Gly Arg Val Ala
    130                 135                 140

Cys Gly Ile Ile Gly Leu Gln Gly
145                 150

<210> SEQ ID NO 71
<211> LENGTH: 152
<212> TYPE: PRT
<213> ORGANISM: Brassica juncea

<400> SEQUENCE: 71

Met Ala Lys Gly Val Ala Val Leu Asn Ser Ser Glu Gly Val Lys Gly
1               5                   10                  15

Thr Ile Phe Phe Thr Gln Glu Gly Asp Gly Ala Thr Thr Val Thr Gly
            20                  25                  30

Thr Val Ser Gly Leu Lys Pro Gly Pro His Gly Phe His Val His Ala

```
              35                  40                  45
Leu Gly Asp Thr Thr Asn Gly Cys Met Ser Thr Gly Pro His Phe Asn
     50                  55                  60

Pro Asp Gly Lys Thr His Gly Ala Pro Glu Asp Ala Asn Arg His Ala
 65                  70                  75                  80

Gly Asp Leu Gly Asn Ile Ile Val Gly Asp Gly Thr Ala Thr Phe
                 85                  90                  95

Thr Ile Thr Asp Ser Gln Ile Pro Leu Thr Gly Pro Asn Ser Ile Val
                100                 105                 110

Gly Arg Ala Val Val His Ala Glu Arg Asp Asp Leu Gly Lys Gly
             115                 120                 125

Gly His Glu Leu Ser Leu Ser Thr Gly Asn Ala Gly Gly Arg Val Ala
         130                 135                 140

Cys Gly Ile Ile Gly Leu Gln Gly
145                 150

<210> SEQ ID NO 72
<211> LENGTH: 152
<212> TYPE: PRT
<213> ORGANISM: Malus domestica

<400> SEQUENCE: 72

Met Val Lys Gly Val Ala Val Leu Gly Ser Ser Glu Gly Val Lys Gly
  1               5                  10                  15

Thr Ile Ser Phe Val Gln Glu Gly Asp Gly Pro Thr Thr Val Thr Gly
                 20                  25                  30

Ser Val Ser Gly Leu Lys Pro Gly Leu His Gly Phe His Val His Ala
             35                  40                  45

Leu Gly Asp Thr Thr Asn Gly Cys Met Ser Thr Gly Pro His Phe Asn
     50                  55                  60

Pro Ala Gly Lys Glu His Gly Ala Pro Glu Asp Glu Leu Arg His Ala
 65                  70                  75                  80

Gly Asp Leu Gly Asn Ile Thr Ala Gly Asp Asp Gly Thr Ala Thr Phe
                 85                  90                  95

Thr Ile Val Asp Lys Gln Ile Pro Leu Ala Gly Pro His Ser Ile Ile
                100                 105                 110

Gly Arg Ala Val Val His Ala Asp Pro Asp Asp Leu Gly Lys Gly
             115                 120                 125

Gly His Glu Leu Ser Lys Ser Thr Gly Asn Ala Gly Gly Arg Val Ala
         130                 135                 140

Cys Gly Ile Ile Gly Leu Gln Gly
145                 150

<210> SEQ ID NO 73
<211> LENGTH: 152
<212> TYPE: PRT
<213> ORGANISM: Potentilla atrosanguinea

<400> SEQUENCE: 73

Met Ala Lys Gly Val Ala Val Leu Ser Ser Ser Glu Gly Val Ala Gly
  1               5                  10                  15

Thr Ile Leu Phe Thr Gln Glu Gly Asp Gly Pro Thr Thr Val Thr Gly
                 20                  25                  30

Asn Ile Ser Gly Leu Lys Pro Gly Leu His Gly Phe His Val His Ala
             35                  40                  45

Leu Gly Asp Thr Thr Asn Gly Cys Met Ser Thr Gly Pro His Phe Asn
```

```
                    50                  55                  60
Pro Ala Gly Lys Glu His Gly Ser Pro Glu Asp Glu Thr Arg His Ala
 65                  70                  75                  80

Gly Asp Leu Gly Asn Ile Thr Val Gly Asp Gly Thr Ala Cys Phe
                 85                  90                  95

Thr Ile Val Asp Lys Gln Ile Pro Leu Thr Gly Pro His Ser Ile Ile
                100                 105                 110

Gly Arg Ala Val Val His Ala Asp Pro Asp Leu Gly Lys Gly
            115                 120                 125

Gly His Glu Leu Ser Lys Ser Thr Gly Asn Ala Gly Gly Arg Ile Ala
            130                 135                 140

Cys Gly Ile Ile Gly Leu Gln Gly
145                 150

<210> SEQ ID NO 74
<211> LENGTH: 152
<212> TYPE: PRT
<213> ORGANISM: Zea mays

<400> SEQUENCE: 74

Met Val Lys Ala Val Ala Val Leu Gly Ser Ser Glu Gly Val Lys Gly
  1               5                  10                  15

Thr Ile Phe Phe Thr Gln Glu Gly Asp Gly Pro Thr Thr Val Thr Gly
                 20                  25                  30

Ser Val Ser Gly Leu Lys Pro Gly Leu His Gly Phe His Val His Ala
                 35                  40                  45

Leu Gly Asp Thr Thr Asn Gly Cys Met Ser Thr Gly Pro His Tyr Asn
 50                  55                  60

Pro Ala Ser Lys Glu His Gly Ala Pro Glu Asp Glu Asn Arg His Ala
 65                  70                  75                  80

Gly Asp Leu Gly Asn Val Thr Ala Gly Ala Asp Gly Val Ala Asn Ile
                 85                  90                  95

Asn Val Thr Asp Ser Gln Ile Pro Leu Thr Gly Pro Asn Ser Ile Ile
                100                 105                 110

Gly Arg Ala Val Val His Ala Asp Pro Asp Leu Gly Lys Gly
            115                 120                 125

Gly His Glu Leu Ser Lys Ser Thr Gly Asn Ala Gly Gly Arg Val Ala
            130                 135                 140

Cys Gly Ile Ile Gly Leu Gln Gly
145                 150

<210> SEQ ID NO 75
<211> LENGTH: 152
<212> TYPE: PRT
<213> ORGANISM: Oryza

<400> SEQUENCE: 75

Met Val Lys Ala Val Ala Val Leu Ala Ser Ser Glu Gly Val Lys Gly
  1               5                  10                  15

Thr Ile Phe Phe Ser Gln Glu Gly Asp Gly Pro Thr Ser Val Thr Gly
                 20                  25                  30

Ser Val Ser Gly Leu Lys Pro Gly Leu His Gly Phe His Val His Ala
                 35                  40                  45

Leu Gly Asp Thr Thr Asn Gly Cys Met Ser Thr Gly Pro His Phe Asn
 50                  55                  60

Pro Thr Gly Lys Glu His Gly Ala Pro Gln Asp Glu Asn Arg His Ala
```

```
                65                  70                  75                  80
Gly Asp Leu Gly Asn Ile Thr Ala Gly Ala Asp Gly Val Ala Asn Val
                    85                  90                  95
Asn Val Ser Asp Ser Gln Ile Pro Leu Thr Gly Ala His Ser Ile Ile
                100                 105                 110
Gly Arg Ala Val Val His Ala Asp Pro Asp Leu Gly Lys Gly
                115                 120                 125
Gly His Glu Leu Ser Lys Thr Thr Gly Asn Ala Gly Arg Val Ala
            130                 135                 140
Cys Gly Ile Ile Gly Leu Gln Gly
145                 150

<210> SEQ ID NO 76
<211> LENGTH: 152
<212> TYPE: PRT
<213> ORGANISM: Potentilla -F

<400> SEQUENCE: 76

Met Ala Lys Gly Val Ala Val Leu Ser Ser Glu Gly Val Ala Gly
1               5                   10                  15
Thr Ile Leu Phe Thr Gln Glu Gly Asp Gly Pro Thr Val Thr Gly
                20                  25                  30
Asn Ile Ser Gly Leu Lys Pro Gly Leu His Gly Phe His Val His Ala
                35                  40                  45
Leu Gly Asp Thr Thr Asn Gly Cys Met Ser Thr Gly Pro His Phe Asn
            50                  55                  60
Pro Ala Gly Lys Glu His Gly Ser Pro Glu Asp Glu Thr Arg His Ala
65                  70                  75                  80
Gly Asp Leu Gly Asn Ile Thr Val Gly Asp Asp Gly Thr Ala Cys Phe
                    85                  90                  95
Thr Ile Val Asp Lys Gln Ile Pro Leu Thr Gly Pro His Ser Ile Ile
                100                 105                 110
Gly Arg Ala Val Val His Ala Asp Pro Asp Leu Gly Lys Gly
                115                 120                 125
Gly His Glu Leu Ser Lys Ser Thr Gly Asn Ala Gly Gly Arg Ile Ala
            130                 135                 140
Cys Gly Ile Ile Gly Leu Gln Gly
145                 150

<210> SEQ ID NO 77
<211> LENGTH: 129
<212> TYPE: PRT
<213> ORGANISM: Potentilla

<400> SEQUENCE: 77

Gln Glu Gly Asp Gly Pro Thr Thr Val Thr Gly Asn Ile Ser Gly Leu
1               5                   10                  15
Lys Pro Gly Leu His Gly Phe His Val His Ala Leu Gly Asp Thr Thr
                20                  25                  30
Asn Gly Cys Met Ser Thr Gly Pro His Phe Asn Pro Ala Gly Lys Glu
            35                  40                  45
His Gly Ser Pro Glu Asp Glu Thr Arg His Ala Gly Asp Leu Gly Asn
        50                  55                  60
Ile Thr Val Gly Asp Asp Gly Thr Ala Cys Phe Thr Ile Val Asp Lys
65                  70                  75                  80
Gln Ile Pro Leu Thr Gly Pro His Ser Ile Ile Gly Arg Ala Val Val
```

```
                     85                  90                  95

Val His Ala Asp Pro Asp Leu Gly Lys Gly Gly His Glu Leu Ser
            100                 105                 110

Lys Ser Thr Gly Asn Ala Gly Gly Arg Ile Ala Cys Gly Ile Ile Gly
            115                 120                 125

Leu

<210> SEQ ID NO 78
<211> LENGTH: 130
<212> TYPE: PRT
<213> ORGANISM: Lantana camara

<400> SEQUENCE: 78

Gln Glu Gly Asp Asp Thr Thr Val Thr Gly Ser Leu Ser Gly Leu
1               5                   10                  15

Lys Pro Gly Gln His Gly Phe His Val His Ala Leu Gly Asp Thr Thr
            20                  25                  30

Asn Gly Cys Met Ser Thr Gly Pro His Phe Asn Pro Gly Gly Lys Glu
        35                  40                  45

His Gly Ala Pro Gly Asp Glu Asn Arg His Ala Gly Asp Leu Gly Asn
    50                  55                  60

Val Thr Val Gly Glu Asp Gly Lys Ala Ser Phe Thr Val Val Asp Lys
65                  70                  75                  80

Gln Ile Pro Leu Thr Gly Pro His Ser Ile Ile Gly Arg Ala Val Val
                85                  90                  95

Val His Ala Asp Pro Asp Leu Gly Lys Gly Gly His Glu Leu Ser
            100                 105                 110

Lys Thr Thr Gly Asn Ala Gly Gly Arg Val Ala Cys Gly Ile Ile Gly
            115                 120                 125

Leu Gln
    130

<210> SEQ ID NO 79
<211> LENGTH: 130
<212> TYPE: PRT
<213> ORGANISM: Curcuma aromatica

<400> SEQUENCE: 79

Gln Glu Gly Asp Gly Pro Thr Thr Val Thr Gly Ser Ile Thr Gly Leu
1               5                   10                  15

Lys Ala Gly Leu His Gly Phe His Val His Ala Leu Gly Asp Thr Thr
            20                  25                  30

Asn Gly Cys Met Ser Thr Gly Pro His Phe Asn Pro Ala Gly Lys Glu
        35                  40                  45

His Gly Ala Pro Glu Asp Val Asn Arg His Ala Gly Asp Leu Gly Asn
    50                  55                  60

Val Thr Ala Ser Glu Asp Gly Ile Val Ala Val Ser Val Val Asp Lys
65                  70                  75                  80

Gln Ile Pro Leu Thr Gly Pro His Ser Ile Ile Gly Arg Ala Val Val
                85                  90                  95

Val His Ala Asp Pro Asp Asp Leu Gly Lys Gly Gly His Glu Leu Ser
            100                 105                 110
```

-continued

```
Lys Ser Thr Gly Asn Ala Gly Gly Arg Ile Ala Cys Gly Ile Ile Gly
        115                 120                 125

Leu Gln
    130
```

METHOD OF CLONING STABLE STRESS TOLERANT SUPEROXIDE DISMUTASE USING UNIVERSAL PRIMERS

INCORPORATION BY REFERENCE OF SEQUENCE LISTING SUBMITTED AS ASCII TEXT FILES VIA EFS-WEB

The Sequence Listing is submitted as an ASCII text file via EFS-WEB, entitled "LALL.P0020US.txt", created on Nov. 17, 2011, and containing 44,875 bytes. The material contained in the above-mentioned ASCII text file is specifically incorporated herein by reference.

FIELD OF INVENTION

The present invention relates to a method of cloning stable stress tolerant superoxide dismutase from diverse plant species using universal primers. The stress parameters include high temperature, pressure and sub zero temperature. The present invention also relates to a method of isolating partial Cu/Zn SOD gene from plant species; *Camellia sinensis, Caragana jubata, Arnebia euchroma, Rheum emodi, Picrorhiza kurrooa, Stevia rebaudiana, Curcuma aromatica, Eragrostis atrovirens, Echinocloa crussgalli, Eleucine indica, Cynodon dactylon, Pennisetum clandistinum, Toona sinensis* and *Lantana camara*.

Gene within the present scope of invention refers to that part of deoxyribonucleic acid (hereinafter, referred to "DNA") that gives rise to messenger ribonucleic acid (hereinafter, referred to "mRNA") and whose product makes a protein. The present invention also relates to a method for amplifying Cu/Zn SOD gene using oligonucleotide primers, from diverse plant species (*Camellia sinensis, Caragana jubata, Arnebia euchroma, Rheum emodi, Picrorhiza kurrooa, Stevia rebaudiana, Curcuma aromatica, Eragrostis atrovirens, Echinocloa crussgalli, Eleucine indica, Cynodon dactylon, Pennisetum clandistinum, Toona sinensis* and *Lantana camara*) from which cloning of Cu/Zn SOD genes has not been reported so far. The present invention also relates to isolating full length cDNA encoding Cu/Zn SOD from *Caragana jubata* and *Curcuma aromatica*. Further, the present invention relates to expressing the isolated cDNAs from *Caragana jubata* and *Curcuma aromatica* in *E. coli* which led to the production of thermostable recombinant SOD enzymes.

BACKGROUND AND PRIOR ART REFERENCES TO THE INVENTION

SOD catalyzes dismutation of superoxide radical (hereinafter, referred to "$O_2^-$.") into hydrogen peroxide and oxygen as per the following redox reaction:

$$2O_2^-.+2H^+=H_2O_2+O_2$$

This reaction is the first enzymatic cellular defense against oxidative stress caused by $O_2^-$.. $O_2^-$. is generated by a number of metabolic perturbations and hence SOD has implications in all those reactions, wherein $O_2^-$. is produced in the amount leading to cellular injury. According to the U.S. Pat. Nos. 6,485,950 and 7,037,697, we have extracted an autoclavable copper/zinc superoxide dismutase (hereinafter referred as Cu/Zn SOD) from *Potentilla atrosanguinea* (hereinafter, referred to "*Potentilla*") which shows activity at sub-zero temperatures. In yet another U.S. patent application Ser. No. 12/315,301, we have cloned Cu/Zn SOD gene from *Potentilla* in *Escherichia coli* (hereinafter, referred to "*E. coli*"). Analysis of Cu/Zn SOD gene sequences from various sources showed maximum variability at 3' and 5' regions with least variability in the middle part of the gene and that can be utilized to synthesize degenerate primers for amplification of Cu/Zn SOD genes. Degenerate primers have been designed from the selected conserved regions of the sequences and used for amplification of Cu/Zn SOD gene from diverse plant species.

Below is given a state of the art knowledge in relation to oligonucleotide primers for amplification of Cu/Zn SOD gene from various sources Reference may be made to document (1) by Liu, J. J., Goh, C., Loh, C., Tay, E. B. H. and Pua, E. C. (Plant Physiol., 1998.116: 867) wherein cDNAs encoding Cu/Zn SOD were cloned from *Brassica juncea*, using degenerate oligonucleotide primers, synthesized from conserved domains of plant Cu/Zn-SOD homologs. However, these forward and reverse primers corresponded to the polypeptides of GC(M/I)STGPH (SEQ ID NO:45) and NAGGR(L/V)AC (SEQ ID NO:46), respectively. These primers were used for amplification of DNA from mustard cDNA library using PCR and an expected 300 bp DNA fragment was amplified.

Reference may be made to document (2) by Banks, G. K., Robinson, A. S., Kwiatowski, J., Ayala, F. J., Scott, M. J. and Kriticou, D. (Genetics, 1995. 140: 697-702) wherein four degenerate primers were used to amplify Cu/Zn SOD from Medfly (*Ceratitis capitata*), which were synthesized from three conserved regions of the known SOD enzyme. However, primer I, II, IIa and IIIb corresponded to the polypeptides of HGFHVH (SEQ ID NO:47), GPHFNP (SEQ ID NO:48), GCGVIG (SEQ ID NO:49), ACGVIG (SEQ ID NO:50) respectively. A 330 bp DNA fragment was amplified with primers I and Mb, while 260 bp fragment was obtained with primers II and IIIb.

Reference may be made to document (3) by Saavedra, N. Y. H., Egly, J. M. and Ochoa, J. L. (Yeast, 1998. 14: 573-581) wherein degenerate primers were used to amplify Cu/Zn SOD from Marine Yeast (*Debaryomyces hansenii*), synthesized from the Cu/Zn SOD protein sequence from yeast (*Saccharomyces cerevisiae*). N-terminal peptide sequences (VS-GVVNFEQSSEEDPT (SEQ ID NO:51)) obtained from pure *Debaryomyces hansenii* Cu/Zn SOD protein showed 81.5% homology with the reported *Saccharomyces cerevisiae* Cu/Zn SOD sequence and hence the N- and C-terminal sequences of the *Saccharomyces cerevisiae* Cu/Zn SOD nucleotide sequence were used to design the degenerate primers (NT1: ATGAA(AG)GCIGTITG (SEQ ID NO:52) (TC) GTIATGACIGG (SEQ ID NO:53) and CT1: TC(AG)TC(TC)TC(AG)TT(TC)TC(AG)TG(GTA)AT(I)ACCAT) (SEQ ID NO:54). An amplified PCR product of 470 bp was obtained using degenerate primers NT1 and CT1.

Reference may be made to document (4) by Plantivaux, A., Furla, P., Zoccola, D., Garello, G., Forcioli, D., Richier, S., Merle, P. L., Tambutte, E., Tambutte, S. and Allemand, D. B (Free Radical Biology & Medicine, 2004. 37:1170-1181) wherein degenerate primers were used to clone two Cu/Zn SOD from sea anemone. Degenerate primers (CuF: GCNG-GNCCNCAYTTYAAYCC (SEQ ID NO:55) and CuR: CCR-CANGCNARNCKNGCNC (SEQ ID NO:56) CNCGRTT-NCC (SEQ ID NO:57)) were designed from the highly conserved regions of the Cu/Zn SOD amino acid sequences from phylogenetically different organisms. These primers were used in RT-PCR and two fragments of approximately 250 bp were amplified.

The Drawbacks are:
1. The oligonucleotide primers reported so far amplified very short region of the gene which do not cover the metal binding domain an essential requirement for the activity of Cu/Zn SOD.
2. The primers which amplify the gene including copper/zinc binding domain were not universal and hence could not be used to amplify the gene.
3. There is no report to show that partial genes cloned through degenerate primers will have SOD activity.
4. There is no report available about isolating the partial Cu/Zn SOD gene from plant species; *Camellia sinensis, Caragana jubata, Arnebia euchroma, Rheum emodi, Picrorhiza kurrooa, Stevia rebaudiana, Curcuma aromatica, Eragrostis atrovirens, Echinocloa crussgalli, Eleucine indica, Cynodon dactylon, Pennisetum clandistinum, Toona sinensis* and *Lantana camara*.
5. Apart from *Potentilla atrosanguinea* no other SOD has been reported which is autoclave stable
6. No Cu/Zn SOD enzyme except from *Potentilla atrosanguinea*, has been reported to function at sub-zero temperature.
7. There is no Cu/Zn SOD gene that is isolated from *Caragana jubata* and *Curcuma aromatica*, and made to express in *E. coli*.

OBJECTS OF THE INVENTION

The main object of the invention is to provide a method of cloning stable stress tolerant superoxide dismutase from diverse plant species using universal primers. It involves a method for cloning functional gene of copper/zinc superoxide dismutases using oligonucleotide primers which obviates the drawbacks of the hitherto known prior art as detailed above.

Another object of the present invention is to design degenerate primers from the selected regions of the sequences of Cu/Zn SOD gene.

Still another object of the present invention is to amplify Cu/Zn SOD gene from diverse plant species using these primers.

Still another object of the present invention is to evaluate the functionality of the partial gene products.

Another object of the present invention is to screen bio resource to identify the SODs having high thermostable properties.

Still another object of the present invention is to identify the genes encoding the novel Cu/Zn SODs from their sources.

Still another object of the present invention is to isolate the full length genes encoding the novel Cu/Zn SODs from their sources.

Still another object of the present invention is to express the cloned genes in heterologous system.

Still another object of the present invention is to evaluate the functionality of the expressed gene products.

The present invention is illustrated in FIGS. 1 to 7 of the drawings accompanying this specification. In the drawings like reference numbers/letters indicate corresponding parts in the various figures.

FIG. 1 represents amplification of Cu/Zn SOD gene from diverse plant species using degenerate primers. Generic names of plant species from which the genes were amplified are written along with the corresponding gels.

Figure 2:
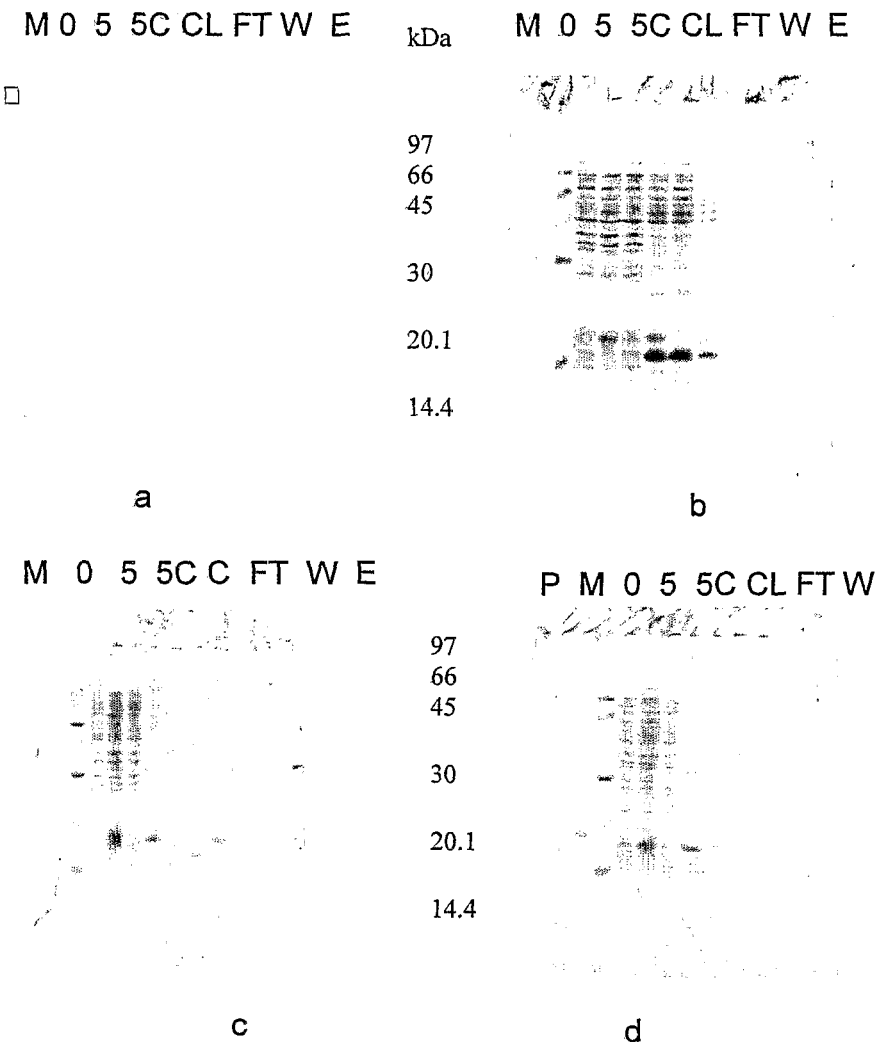

FIG. 2 represents the gels showing sodium dodecyl sulfate-polyacrylamide gel electrophoresis (hereinafter, referred to "SDS-PAGE") of fractions obtained during purification of partial Cu/Zn SOD proteins. SDS PAGE of fractions obtained during purification of recombinant partial Cu/Zn SODs using Ni-NTA columns. (a) Protein fractions obtained from recombinant *Potentilla atrosanguinea* Cu/Zn SOD, (b) protein fractions obtained from recombinant *Potentilla atrosanguinea* partial Cu/Zn SOD, (c) protein fractions obtained from recombinant *Lantana camara* partial Cu/Zn SOD. (d) protein fractions obtained from recombinant *Curcuma aromatica* partial Cu/Zn SOD. Lanes CL, FT, W and E represent clear lysate, flow though, wash and eluted protein fractions, respectively. Lane M represents molecular weight marker proteins (GE Healthcare: LMW containing Phophorylase b, 97 000; Albumin bovine serum, 66 000; Ovalbumin, 45 000; Carbonic anhydrase, 30 000; Trypsin inhibitor, 20 100; α-Lactalbumin 14 400 Da). Lanes 0 and 5 represent induced cultures whereas, 5C is control (without IPTG addition) culture at 5 h. Lane P represents purified recombinant *Potentilla* Cu/Zn SOD.

Figure 3:
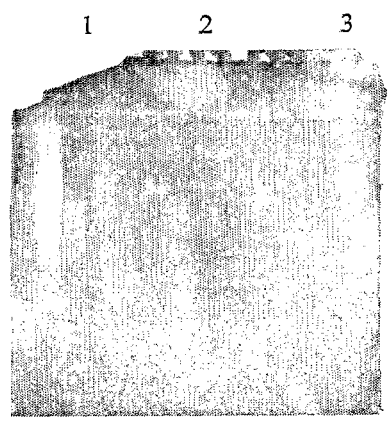

FIG. 3 represents In-gel assay for SOD activity of fractions obtained from recombinant *E. coli* cultures. Lanes 1, 2 and 3 are purified protein fractions of partial Cu/Zn SOD from *Potentilla atrosanguinea, Curcuma aromatica* and *Lantana camara*, respectively.

Figure 4:
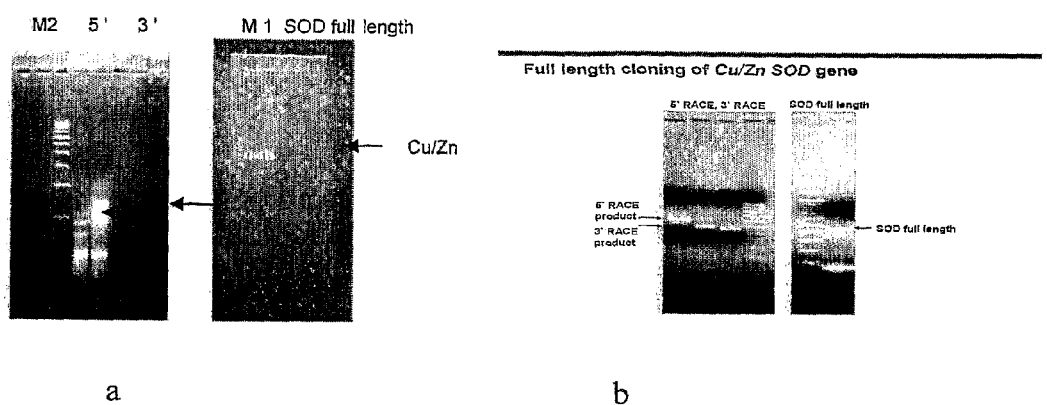

FIG. 4 represents PCR amplification of 5' and 3' RACE fragments and full length amplification of Cu/Zn SOD cDNAs from (a) *Curcuma aromatica* and, (b) *Caragana jubata* by RACE PCR. Lane M1: represents 100 bp ladder and Lane M2: represents 500 bp ladder.

Figure 5:
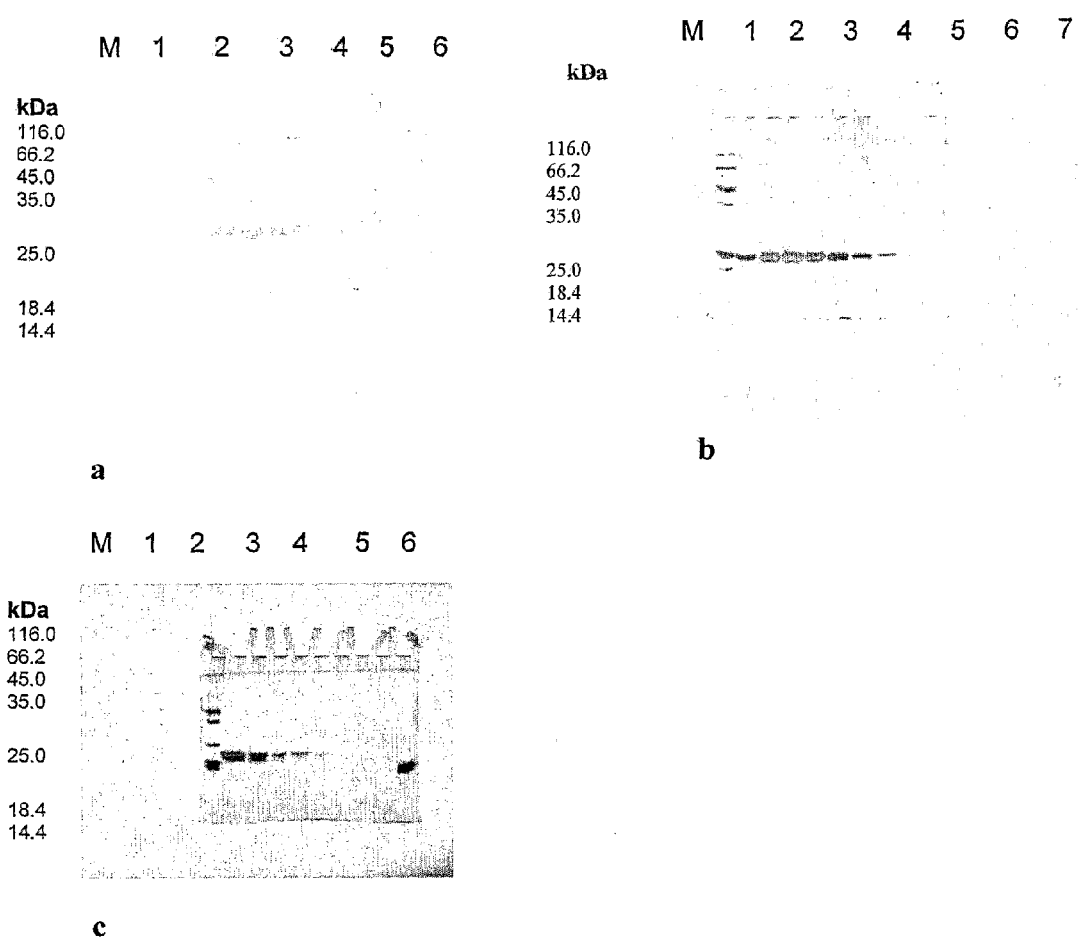

FIG. 5 represents: SDS-PAGE analysis of purified recombinant Cu/Zn SODs from (a) *Potentilla atrosanguinea* (b) *Caragana jubata* (c) *Curcuma aromatica*. Lane M represents molecular weight marker (fermentas). 14.4: Lysozyme (chicken egg white). 18.4: lactoglobulin (bovine milk). 25: REase Bsp 981 (*E. coli*). 35: Lactate dehydrogenase (porcine muscle). 45.0: Ovalbumin (Chicken egg white). 66.2: Bovine serum albumin (bovine plasma). 116.0: β-galactosidase (*E. coli*.). Lanes 1, 2, 3, 4, 5, 6, and 7 represent purified protein fractions.

Figure 6:
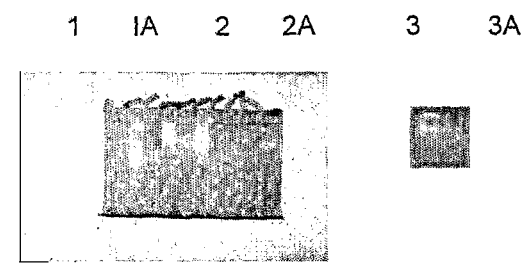

FIG. 6 represents In-gel assay for SOD activity of recombinant Cu/Zn SODs. from *Potentilla atrosanguinea, Curcuma aromatica* and *Caragana jubata*. Lanes 1, 2 and 3 represent unautoclaved recombinant Cu/Zn SOD fractions from *Potentilla atrosanguinea, Curcuma aromatica* and *Caragana jubata*. Lanes 1A, 2A and 3A represent their respective autoclaved fractions. Equal quantity in terms of volume was loaded of autoclaved and unautoclaved fractions.

Figure 7:
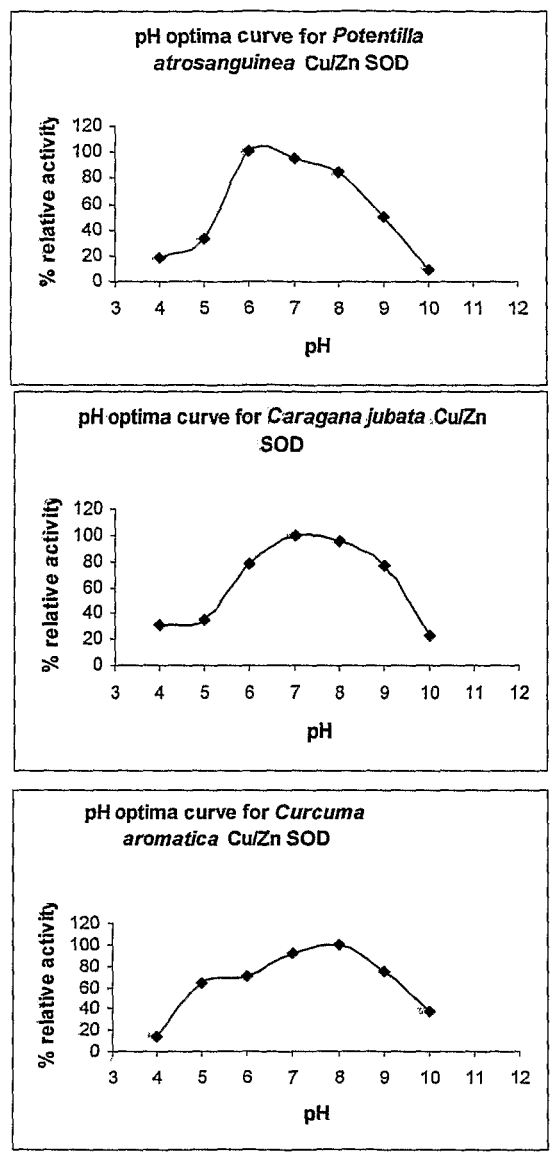

FIG. 7 represents effect of pH on activities of *Potentilla atrosanguinea, Caragana jubata* and *Curcuma aromatica* Cu/Zn SODs.

SUMMARY OF THE INVENTION

Accordingly the present invention provides a method of cloning stable stress tolerant superoxide dismutase from diverse plant species using universal primers.

DETAILED DESCRIPTION OF THE INVENTION

The gene sequence reported in U.S. patent application Ser. No. 12/315,301 was compared with the Cu/Zn SOD gene sequences reported from other plants [*Arabidopsis* (accession no. NM_100757), *Brassica* (accession no. AY970822), *Malus* (accession no. AY646367), *Potentilla* (accession no. EU532614), *Oryza* (accession no. D01000), *Zea* (accession no. NM_001112234)], to figure out the conserved region, through use of alignment programs routinely utilized in the art, e.g., those made available in public sequence databases. The primers were designed from the selected regions as indicated in Table 1.

TABLE 1

The oligonucleotide Primer Sets used for amplifying Cu/Zn SOD gene. The letter F and R in sequence ID represent forward primer and reverse primer, respectively.

| Primer Set No. | Primer SEQ ID | Oligonucleotide primer sequences |
|---|---|---|
| Set 1 | 24 | 5'CAGGAAGGAGATGG(C/T)CCAAC(A/C) 3' |
|  | 25 | 5' (C/T)TGAA(A/G)(A/G)CC(A/G)AT(G/A/C)CCACAAGC 3' |
| Set 2 | 26 | 5'TC(A/T)AC(C/T)GG(G/A/T)CC(A/G)CA(C/T)TA(C/T)AAT 3' |
|  | 27 | 5' (C/T)TGAA(A/G)(A/G)CC(A/G)AT(G/A/C)CCACAAGC 3' |

In an embodiment of the present invention it provides set of degenerate primer pairs useful for amplifying stress tolerant superoxide dismutase from diverse plant species wherein the said set comprises of:

a.
SEQ ID No. 24 & 25.
Forward primer =
5'CAGGAAGGAGATGG(C/T)CCAAC(A/C) 3'

Reverse primer =
5' (C/T)TGAA(A/G)(A/G)CC(A/G)AT(G/A/C)CCACAAGC 3' b.
SEQ ID No. 26 & 27.
Forward primer =
5' TC(A/T)AC(C/T)GG(G/A/T)CC(A/G)CA(C/T)TA(C/T)AAT 3'

Reverse primer =
5' (C/T)TGAA(A/G)(A/G)CC(A/G)AT(G/A/C)CCACAAGC 3' wherein the said primers are used alone or in combination,

In yet another embodiment of the present invention, set of primer pairs stated above is characterized in:
 i. length of the said forward primer (SEQ ID No. 24) is 21 mer and for the reverse primer (SEQ ID No. 25) is 21 mer,
 ii. G+C content is in range of 38 to 62%,
 iii. Tm is in range of 49° C. to 58° C.,
 iv. annealing temperature is preferably in the range of 53° C. to 58° C. and optimal annealing temperature for SOD detection is about 55° C.,
 v. length of the said forward primer (SEQ ID No. 26) is 21 mer and for the reverse primer (SEQ ID No. 27) is 21 mer,
 vi. G+C content is in range of 33% to 62%,
 vii. Tm is in range of 47° C. to 56° C.,
 viii. annealing temperature is preferably in the range of 52° C. to 58° C. and optimal annealing temperature for SOD detection is about 55° C., In yet another embodiment of the present invention, the primer pair having Seq ID No. 24 & 25 is useful in amplifying 390 bp gene product which covered the copper/zinc binding domains essential for SOD activity.

In yet another embodiment of the present invention, the primer pair having Seq ID No. 26 & 27 is useful in amplifying 280 bp gene product, In an embodiment of the present invention, a method of cloning stable stress tolerant superoxide dismutase from diverse plant species comprising:
 a. isolating the total RNA from leaf tissue and synthesizing its complementary DNA,
 b. designing and preparing universal primer sets of Cu/Zn SOD gene selected from the group consisting of Seq ID No. 24-27,
 c. amplifying Cu/Zn SOD gene using the primer set obtained in step b,
 d. ligating the amplified product obtained in step c into a vector to yield a recombinant plasmid,
 e. transforming the recombinant plasmid obtained in step d into suitable cell for expression,
 f. purifying the stable stress tolerant superoxide dismutase.

In another embodiment of the present invention, the diverse plant species are selected from the group consisting of Camellia sinensis, Caragana jubata, Arnebia euchroma, Rheum emodi, Picrorhiza kurrooa, Stevia rebaudiana, Curcuma aromatica, Eragrostis atrovirens, Echinocloa crussgalia, Eleucine indica, Cynodon dactylone, Pennisetum clandistinum, Toona sinesis and Lantana camara.

In another embodiment of the present invention, the stress parameters are selected from the group consisting of high temperature, pressure and sub-zero temperature.

In yet another embodiment of the present invention, the high temperature used is in the range of 100° C. to 121° C.

In yet another embodiment of the present invention, the pressure used is in the range of 14 pounds per square inch (psi) to 15 psi.

In yet another embodiment of the present invention, the sub-zero temperature used is in the range of 0° C. to minus 10° C.

In yet another embodiment of the present invention, the PCR involves initial denaturation at 94° C. for 3 min, followed by 94° C. for 30 sec, 55° C. for 45 sec and 72° C. for 1 min for 35 cycles and then a final extension at 72° C. for 7 min.

In yet another embodiment of the present invention, the partial Cu/Zn SOD gene from plant species are selected from the group consisting of Camellia sinensis, Caragana jubata, Arnebia euchroma, Rheum emodi, Picrorhiza kurrooa, Stevia rebaudiana, Curcuma aromatica, Eragrostis atrovirens, Echinocloa crussgalli, Eleucine indica, Cynodon dactylon, Pennisetum clandistinum, Toona sinesis and Lantana camara was isolated selected from the group consisting of Seg ID no. 1-16.

In yet another embodiment of the present invention, the full length Cu/Zn SOD cDNA sequences are amplified from diverse plant species selected from the group consisting of Camellia sinensis, Caragana jubata, Arnebia euchroma, Rheum emodi, Picrorhiza kurrooa, Stevia rebaudiana, Curcuma aromatica, Eragrostis atrovirens, Echinocloa crussgalli, Eleucine indica, Cynodon dactylon, Pennisetum clandistinum, Toona sinesis and Lantana camara having sequences selected from the group consisting of SEQ ID no. 20 & 22.

In yet another embodiment of the present invention, the amplified product is useful as a probe to detect expression of Cu/Zn SOD genes in organisms selected from the group comprising of plants, animals and microbial system and the like.

In yet another embodiment of the present invention, the sequences are selected from the group consisting of SEQ ID No: 1 to SEQ ID No. 20 and SEQ ID No. 22 is useful for developing stress tolerant transgenic plants.

In yet another embodiment of the present invention, sequences are selected from the group consisting of SEQ ID No: 1 to SEQ ID No. 20 and SEQ ID No. 22 is useful for amplifying the upstream promoter regions of the Cu/Zn SOD gene.

In yet another embodiment of the present invention, sequences are selected from the group consisting of SEQ ID No: 1 to SEQ ID No. 20 and SEQ ID No. 22 is useful for identifying and cloning of intron region(s) of Cu/Zn SOD gene.

In yet another embodiment of the present invention, sequences are selected from the group consisting of SEQ ID No: 1 to SEQ ID No. 20 and SEQ ID No. 22 is useful for synthesizing SOD proteins.

In yet another embodiment of the present invention, sequences are selected from the group consisting of SEQ ID No: 1 to SEQ ID No. 20 and SEQ ID No. 22 is useful for raising antibodies in the animals selected from the group consisting of rabbit, goat, and other animals used for similar purposes.

In yet another embodiment of the present invention, stress tolerant superoxide dismutase from diverse plant species is prepared by the above stated method.

In yet another embodiment of the present invention, a kit for PCR based detection and identification of stress tolerant superoxide dismutase from diverse plant species is described which comprises of:

a. set of primer pairs as described above,
b. providing suitable buffers and reagents,
c. providing instruction manual for carrying out detection and identification of stress tolerant superoxide dismutase from diverse plant species.

In yet another embodiment of the present invention, these partial cDNA sequences of Cu/Zn SOD gene were ligated into a vector to yield a recombinant plasmid, which upon transfer into a suitable *E. coli* host resulted into a clone. Vector, in the present invention refers to a replicon used for the transformation of foreign DNA and take the form of a circular plasmid DNA that shows resistance to a given antibiotic. The genes were sequenced and analyzed, comprising the sequences set forth in SEQ ID No. 1-16.

In yet another embodiment of the present invention, the partially amplified Cu/Zn SOD fragments from *Potentilla atrosanguinea, Lantana camara* and *Curcuma aromatica* were cloned in a plasmid vector containing inducible promoter and expressed in *E. coli*. The expressed Cu/Zn SOD proteins were purified and tested for their activity and autoclave stability.

In yet another embodiment of the present invention, primers were designed from the sequences set forth in SEQ ID No: 4, SEQ ID No: 9, and the "rapid amplification of cDNA ends technique" (hereinafter, referred as RACE) was employed to isolate 3' and 5' ends of SOD gene to clone the full length cDNA from *Caragana jubata* and *Curcuma aromatica*.

In yet another embodiment of the present invention, the full length Cu/Zn SOD cDNAs from *Caragana jubata* and *Curcuma aromatica* and *Lantana camara* were cloned in pGEMT-Easy vector.

In an embodiment of the present invention, various plant species [growing naturally at Palampur, Himachal Pradesh area or maintained under controlled conditions in the Institute, after bringing from high altitude regions of Western Himalaya] were screened for the presence of SOD, which retains their SOD activity at high temperature and/or autoclaving. The species screened included the plants belonging to dicotyledouns group [*Lantana camara* (Verbenaceae); *Potentilla atrosanguinea* (Rosaceae); *Arnebia euchroma* (Boraginaceae); *Stevia rebaudiana* (Asteraceae); *Camellia sinensis* (Theaceae); *Caragana jubata* (Fabaceae); *Rheum emodi* (Polygonaceae); *Picrorhiza kurrooa* (Plantaginaceae); *Toona sinensis* (Meliaceae)] as well as the monocotyledonous plants species [*Eleucine indica*; (Poaceae); *Cynodon dactylon* (Poaceae); *Echinochloa crus-galli* (Poaceae); *Pennisetum clandestinum* (Poaceae); *Eragrostis atrovirens* (Poaceae); *Curcuma aromatica* (Zingiberaceae)].

In another embodiment of the present invention, RNA from plants showing SOD activity at high temperatures (*Caragana jubata, Curcuma aromatica*) was isolated and cDNA was synthesized.

In yet another embodiment of the present invention, using degenerate primers partial SOD gene fragments from *Caragana jubata* and *Curcuma aromatica* were amplified.

In yet another embodiment of the present invention, the amplified gene fragments were sequenced and searched for homologies using BLAST tool.

In yet another embodiment of the present invention, full length cDNAs of the SODs from *Caragana jubata* and *Curcuma aromatica* were amplified.

In yet another embodiment of the present invention, the cloned full length cDNAs of *Caragana jubata* and *Curcuma aromatica* were cloned in pQE-30 UA expression vector.

In yet another embodiment of the present invention, the cloned full length cDNAs cloned in pQE-30 UA vector were expressed and induced using IPTG.

In yet another embodiment of the present invention, full length Cu/Zn SOD cDNA of *Potentilla atmsanguinea* (U.S. application Ser. No. 12/315,301) was expressed and induced using IPTG.

In yet another embodiment of the present invention, the expressed proteins were purified using affinity based chromatography.

In yet another embodiment of the present invention, the purified recombinant SOD proteins were assayed for thermostability and autoclave stability.

In yet another embodiment of the present invention, the purified recombinant SOD proteins were assayed for the activity at different temperatures ranging from −10° C. to +10° C.

The following examples are given by way of illustration of the working of the invention in actual practice and should not be construed to limit the scope of the present invention in any way.

Example-1

Designing of Oligonucleotide Primers:

Degenerate oligonucleotide primers were designed from the conserved regions of the Cu/Zn SOD gene reported from various plants. The sequences were aligned using Multiple Sequence Alignment by CLUSTALW software programme available at http://align.genome.jp and primers were designed using oligonucleotide properties calculator (http://www.basic.northwestern.edu/biotools/oligocalc.html) (Table 1). Oligonucleotide primers were synthesized from Microsynth (Switzerland).

Comparison of various Cu/Zn SOD nucleotide sequences. Regions of complete homology are indicated with asterisks. The sequences used for designing primers are given in Table 1.

```
Arabidopsis  ATGGCGAAAGGAGTTGCAGTTTTGAACAGCAGTGAGGGTGTTACGGGGACTATCTTTTTC  (SEQ ID NO: 58)
Brassica     ATGGCCAAGGGAGTTGCAGTTTTGAACAGCAGTGAGGGTGTTAAGGGGACTATCTTCTTC  (SEQ ID NO: 59)
Malus        ATGGTGAAGGGTGTTGCTGTTCTCGGCTCCAGTGAGGGCGTTAAAGGAACCATCAGCTTT  (SEQ ID NO: 60)
Potentilla   AFGGCAAAGGGCGTTGCTGTACTTAGCTCCAGTGAGGGTGTTGCTGGAACTATCCTCTTT  (SEQ ID NO: 61)
Pisum        ATGGTGAAGGCTGTGGCAGTTCTTAGTAACAGTAACGAAGTCTCGGGTACTATTAACTTC  (SEQ ID NO: 62)
Zea_mays     ATGGTGAAGGCTGTTGCTGTGCTGGGTAGCAGCGATGGTGTCAAGGGCACCATCTTTTTC  (SEQ ID NO: 63)
             ****  **  **  **  **     ***  *   **    **  **  **     **

Arabidopsis  ACCCAGGAAGGCGATGGTGTGACCACTGTGAGTGGAACAGTTTCTGGCCTTAAGCCTGGT  (SEQ ID NO: 58)
Brassica     ACCCAGGAAGGAGATGGTGCCACAACTGTGACTGGAACTGTTTCTGGTCTTAAACCTGGT  (SEQ ID NO: 59)
Malus        GTCCAGGAGGGAGATGGCCCAACTACTGTGACTGGAAGTGTCTCTGGCCTCAAGCCTGGA  (SEQ ID NO: 60)
Potentilla   ACCCAAGAGGGAGATGGCCCAACTACTGTGACCGGAAACATTTCTGGCCTCAAGCCTGGG  (SEQ ID NO: 61)
Pisum        AGTCAGGAGGGAAATGGTCCAACCACTGTAACTGGAACTCTTGCTGGTCTTAAGCCTGGC  (SEQ ID NO: 62)
Zea_mays     ACCCAAGAGGGAGATGGCCCTACCGCTGTCACTGGAAGTGTCTCTGGCCTCAAGCCTGGC  (SEQ ID NO: 63)
             **  **  **  ****   **  ****  *  ****  *  ****  **  **  *****

Arabidopsis  CTTCATGGTTTCCATGTCCATGCTCTTGGTGACACCACTAACGGTTGCATGTCTACTGGT  (SEQ ID NO: 58)
Brassica     CCCCATGGTTTCCATGTCCATGCTCTTGGTGACACCACCAACGGTTGCATGTCTACCGGT  (SEQ ID NO: 59)
Malus        CTTCATGGTTTCCATGTCCATGCTCTTGGAGACACAACAAACGGTTGCATGTCAACTGGG  (SEQ ID NO: 60)
Potentilla   CTTCATGGTTTCCATGTTCATGCTCTTGGGGACACAACCAATGGTTGCATGTCAACTGGA  (SEQ ID NO: 61)
Pisum        CTCCACGGCTTCCATATCCAFGCCTTGGGAGACACCACAAACGGTTGCATTTCAACTGGA  (SEQ ID NO: 62)
Zea_mays     CTCCATGGGTTCCATGTACATGCACTTGGTGACACCACCAATGGATGCATGTCAACTGGA  (SEQ ID NO: 63)
             *  **  **  ******  *****  **  **  *****  **  **  *****  ** **

Arabidopsis  CCACATTTCAACCCCGATGGTAAAACACACGGTGCCCCTGAGGATGCTAATCGACATGCT  (SEQ ID NO: 58)
Brassica     CCACATTTCAACCCTGATGGTAAAACCCACGGTGCACCCGAGGATGCTAATCGTCATGCT  (SEQ ID NO: 59)
Malus        CCACACTTCAATCCTGCTGGAAAAGAGCATGGTGCCCCTGAAGATGAGCTTCGCCATGCT  (SEQ ID NO: 60)
Potentilla   CCACATTTCAATCCTGCTGGCAAAGAGCATGGGTCTCCTGAAGATGAGACTCGTCATGCT  (SEQ ID NO: 61)
Pisum        CCACATITCAATCCTAATGGGAAGGAACATGGTGCCCCTGAGGATGAGACTAGACATGCT  (SEQ ID NO: 62)
Zea_mays     CACGACTACAATCCTGCGAGCAAGGAGCATGGGGCACCAGAAGATGAGAACCGCCATGCC  (SEQ ID NO: 63)
              *  *  ***  **   *  **  **  **  **  *  ****    *  *****

Arabidopsis  GGTGATCTAGGAAACATCACTGTTGGAGATGATGGAACTGCCACCTTCACAATCACTGAT  (SEQ ID NO: 58)
Brassica     GGAGATCTAGGAAACATCATTGTTGGGGATGATGGAACTGCCACCTTCACAATCACTGAC  (SEQ ID NO: 59)
Malus        GGCGATCTTGGAAACATCACTGCTGGGGACGATGGAACTGCAACCTTCACGATTGTTGAC  (SEQ ID NO: 60)
Potentilla   GGTGATCTTGGAAATATCACTGTTGGGGATGACGGAACTGCTTGCTTCACAATTGTTGAC  (SEQ ID NO: 61)
Pisum        GGTGATTTAGGAAATATCAATGTTGGTGATGATGGAACTGTAAGCTTCACCATTACTGAC  (SEQ ID NO: 62)
Zea_mays     GGTGATCTTGGAAATGTGACAGCTGGAGCAGATGGTGTTGCTAATATCAATGTCACTGAC  (SEQ ID NO: 63)
             **  ***  *  *****  *  *  ***  *  **  **  **     ***  *  ***

Arabidopsis  TGCCAGATTCCTCTTACTGGACCAAACTCTATTGITGGTAGGGCTGTTGTTGTCCATGCA  (SEQ ID NO: 64)
Brassica     AGCCAGATTCCTCTTACTGGACCAAACTCTATTGTAGGAAGGGCTGTTGTTGTCCATGCA  (SEQ ID NO: 65)
Malus        AAGCAGATTCCTCTCGCTGGACCACACTCTATCATTGGTAGGGCGGTTGTTGTCCACGCA  (SEQ ID NO: 66)
Potentilla   AAACAGATTCCTCTCACTGGACCACACTCTATCATTGGTAGGGCTGTTGTTGTCCATGCA  (SEQ ID NO: 67)
Pisum        AACCATATCCCTCTCACTGGAACAAACTCCATCATAGGAAGGGCTGTTGTTGTCCATGCC  (SEQ ID NO: 68)
Zea_mays     AGCCAGATCCCACTGACTGGGCCAAACTCAATCATTGGCAGAGCTGTTGTTGTTCACGCT  (SEQ ID NO: 69)
             **  **  **  **  ****  **  ****  *  **  **  **  ********  **  **

Arabidopsis  GACCCTGATGACCTCGGAAAGGGAGGCCATGAACTCAGCCTGGCTACTGGAAACGCAGGC  (SEQ ID NO: 64)
Brassica     GACCGTGATGACCTTGGAAAGGGAGGCCATGAACTCAGCTTGTCTACTGGAAATGCAGGA  (SEQ ID NO: 65)
Malus        GACCCTGATGACCTTGGCAAGGGTGGACATGAGCTTAGCAAATCCACAGGAAATGCTGGT  (SEQ ID NO: 66)
Potentilla   GATCCTGATGACCTTGGCAAGGGTGGACATGAGCTTAGCAAATCCACTGGAAATGCTGGT  (SEQ ID NO: 67)
Pisum        GATCCTGATGATCTTGGGAAGGTGGTCACGAGCTTAGCAAAACTACTGGAAATGCTGGT  (SEQ ID NO: 68)
Zea_mays     GATCCTGATGATCITGGAAAGGGTGGGCACGAGCTTAGCAAGAGCACTGGAAACGCGGGT  (SEQ ID NO: 69)
             **  *  ******  **  **  **  **  **  **  **  ***    **  *****  **  **

Arabidopsis  GGCCGTGTTGCTTGCGGCATCATTGGTCTCCAGGGCTAA  (SEQ ID NO: 64)
Brassica     GGCCGTGTTGCTTGTGGTATTATTGGTCTTCAGGGCTAA  (SEQ ID NO: 65)
Malus        GGCAGGGTGGCTTGCGGTATTATTGGTCTGCAAGGATGA  (SEQ ID NO: 66)
Potentilla   GGCAGGATAGCTTGTGGTATTATTGGCCTTCAAGGATGA  (SEQ ID NO: 67)
Pisum        GGCAGAGTAGCTTGTGGTATTATTGGGTTGCAAGGATAG  (SEQ ID NO: 68)
Zea_mays     GGCCGTGTTGCTTGTGGGATCATTGGACTCCAGGGCTGA  (SEQ ID NO: 69)
             ***  *  *  *****  **  **  *****  *  **  **  *
```

Alignment of the deduced amino acid sequences used for designing of primers. Regions of complete homology are indicated with asterisks. Selected regions used for designing the primers are Table 1.

```
Arabidopsis  MAKGVAVLNSSEGVTGTIFFTQEGDGVTTVSGTVSGLKPGLHGFHVHALGDTTNGCMSTG  (SEQ ID NO: 70)
Brassica     MAKGVAVLNSSEGVKGTIFFTQEGDGATTVTGTVSGLKPGPHGFHVHALGDTTNGCMSTG  (SEQ ID NO: 71)
Malus        MVKGVAVLGSSEGVKGTISFVQEGDGPTTVTGSVSGLKPGLHGFHVHALGDTTNGCMSTG  (SEQ ID NO: 72)
Potentilla   MAKGVAVLSSSEGVAGTILFTQEGDGPTTVTGNISGLKPGLHGFHVHALGDTTNGCMSTG  (SEQ ID NO: 73)
Zea          MVKAVAVLGSSEGVKGTIFFTQEGDGPTTVTGSVSGLKPGLHGFHVHALGDTTNGCMSTG  (SEQ ID NO: 74)
Oryza        MVKAVAVLASSEGVKGTIFFSQEGDGPTSVTGSVSGLKPGLHGFHVHALGDTTNGCMSTG  (SEQ ID NO: 75)
             *.*.**** ***** *** * ****** *.*.*.****** ********************
```

-continued

```
Arabidopsis  PHFNPDGKTHGAPEDANRHAGDLGNITVGDDGTATFTITDCQIPLTGPNSIVGRAVVVHA  (SEQ ID NO: 70)
Brassica     PHFNPDGKTHGAPEDANRHAGDLGNIIVGDDGTATFTITDSQIPLTGPNSIVGRAVVVHA  (SEQ ID NO: 71)
Malus        PHFNPAGKEHGAPEDELRHAGDLGNITAGDDGTATFTIVDKQIPLAGPHSIIGRAVVVHA  (SEQ ID NO: 72)
Potentilla   PHFNPAGKEHGSPEDETRHAGDLGNITVGDDGTACFTIVDKQIPLTGPHSIIGRAVVVHA  (SEQ ID NO: 73)
Zea          PHYNPASKEHGAPEDENRHAGDLGNVTAGADGVANINVTDSQIPLTGPNSIIGRAVVVHA  (SEQ ID NO: 74)
Oryza        PHFNPTGKEHGAPQDENRHAGDLGNITAGADGVANVNVSDSQIPLTGAHSIIGRAVVVHA  (SEQ ID NO: 75)
             **.**.* **:*.: ********:.* **.*..:* ****:*.:**:********

Arabidopsis  DPDDLGKGGHELSLATGNAGGRVACGIIGLQG                              (SEQ ID NO: 70)
Brassica     ERDDLGKGGHELSLSTGNAGGRVACGIIGLQG                              (SEQ ID NO: 71)
Malus        DPDDLGKGGHELSKSTGNAGGRVACGIIGLQG                              (SEQ ID NO: 72)
Potentilla   DPDDLGKGGHELSKSTGNAGGRIACGIIGLQG                              (SEQ ID NO: 73)
Zea          DPDDLGKGGHELSKSTGNAGGRVACGIIGLQG                              (SEQ ID NO: 74)
Oryza        DPDDLGKGGHELSKTTGNAGGRVACGIIGLQG                              (SEQ ID NO: 75)
             :*********** :******:*********
```

Alignment of deduced amino acid sequences of Cu/Zn SOD cloned from *Potentilla atrosanguinea* (SEQ ID NO:1), *Curcuma aromatica* (SEQ ID NO:9), and *Lantana camara* (SEQ ID NO:16) and expressed in *E. coli*. The copper/zinc binding residues are shaded (i. copper binding residues: H45, H47, H62, H119; ii. zinc binding residues: H62, H70, H79; and D82). *Potentilla*-F denotes full length Cu/Zn SOD cDNA cloned from *Potentilla atrosanguinea* and reported in U.S. patent application Ser. No. 12/315,301. Amino acids are represented as standard single letter abbreviations.

```
                                                                      (SEQ ID NO: 76)
Potentilla-F  MAKGVAVLSSSEGVAGTILFTQEGDGPTTVTGNISGLKPGLHGFHVHALGDTTNGCMSTG (SEQ ID NO: 77)
Potentilla    --------------------QEGDGPTTVTGNISGLKPGLHGFHVHALGDTTNGCMSTG (SEQ ID NO: 78)
Lantana       --------------------QEGDDTTTVTGSLSGLKPGQHGFHVHALGDTTNGCMSTG (SEQ ID NO: 79)
Curcuma       --------------------QEGDGPTTVTGSITGLKAGLHGFHVHALGDTTNGCMSTG

****..*****.::***.* *******************

(SEQ ID NO: 76)
Potentilla-F  PHFNPAGKEHGSPEDETRHAGDLGNITVGDDGTACFTIVDKQIPLTGPHSIIGRAVVVHA (SEQ ID NO: 77)
Potentilla    PHFNPAGKEHGSPEDETRHAGDLGNITVGDDGTACFTIVDKQIPLTGPHSIIGRAVVVHA (SEQ ID NO: 78)
Lantana       PHFNPGGKEHGAPGDENRHAGDLGNVTVGEDGKASFTVVDKQIPLTGPHSIIGRAVVVHA (SEQ ID NO: 79)
Curcuma       PHFNPAGKEHGAPEDVNRHAGDLGNVTASEDGIVAVSVVDKQIPLTGPHSIIGRAVVVHA

*****.*****:* *.********:*..:**....::*******************
                                                                      (SEQ ID NO: 76)
Potentilla-F  DPDDLGKGGHELSKSTGNAGGRIACGIIGLQG
                                                                      (SEQ ID NO: 77)
Potentilla    DPDDLGKGGHELSKSTGNAGGRIACGIIGL--
                                                                      (SEQ ID NO: 78)
Lantana       DPDDLGKGGHELSKTTGNAGGRVACGIIGLQ-
                                                                      (SEQ ID NO: 79)
Curcuma       DPDDLGKGGHELSKSTGNAGGRIACGIIGLQ-
              ************** :******:*******
```

Example-2

RNA Isolation, Quantification of RNA and Gel-Electrophoresis:

Ribonucleic acid (hereinafter, referred to "RNA") from young leaf tissue of *Potentilla* was isolated using iRIS Plant RNA Kit (Ghawana et al., U.S. application Ser. No. 12/295,001). Leaf tissue (100 mg) was ground in liquid nitrogen to fine powder using pre-chilled pestle and mortar. Solution I (2 ml) was added to the frozen powder and ground the mixture while still frozen (allow thawing with intermittent grinding) and thawed it completely. Solution II (800 µl) was added and ground for a while. Resulting homogenate was transferred to a 2 ml microcentrifuge tube and left undisturbed for 5 min at room temperature. Chloroform (200 µl) was added to each tube, vortexed briefly and left undisturbed for 10 min at room temperature. Centrifuged at 13,000 rpm for 10 min at 4° C. Transferred upper aqueous phase to a fresh tube (avoid contamination with interphase). Isopropanol (0.6 volume) was added, vortexed briefly and left undisturbed for 10 min at room temperature. Centrifuged at 13,000 rpm for 10 min at 4° C. Washed the RNA pellet with 70% ethanol (in DEPC-treated autoclaved water) by vortexing briefly followed by centrifugation at 13,000 rpm. Air dried the samples for 10-15 min and dissolved the pellet in 20-30 µl of DEPC-treated autoclaved water. RNA was quantified by measuring absorbance at 260 nm and the purity was monitored by calculating the ratio of absorbance measured at 260 and 280 nm. A value >1.8 at 260/280 nm was considered ideal for the purity of RNA used in the present investigation. The formula used to calculate RNA concentration and yield was as follows:

Concentration of RNA (µg/ml)=$A_{260}$(absorbance at 260 nm)×40×dilution factor.

Total yield (µg)=concentration×volume of stock RNA sample.

To check the integrity of RNA, 5-6 µg of RNA in 4.5 µl of DEPC treated autoclaved water was diluted with 15.5 µl of M1 solution (2 µl of 5×MOPS buffer, 3.5 µl of formaldehyde, and 10 µl of formamide [5×MOPS buffer: 300 mM sodium acetate, 10 mM MOPS (3-[N-morpholino]propanesulfonic acid), 0.5 mM ethylene diamine tetra-acetic acid (EDTA)] and incubated for 15 min at 65° C. RNA was loaded onto 1.0% formaldehyde agarose-gel after adding 2 µl of formaldehyde-gel loading buffer [50% glycerol, 1 mM EDTA (pH, 8.0), 0.25% bromophenol blue, 0.25% xylene cyanol FF], and electrophoresed at 72 volts in 1×MOPS buffer (60 mM sodium acetate, 2 mM MOPS, 0.1 mM EDTA), (Sambrook, J., Fritsch, E. F. and Maniatis, T. 1989. Molecular Cloning: A Laboratory Manual, Cold Spring Harbor Laboratory Press, Plainview, N.Y.).

Example-3

Synthesis of Complementary DNA (Hereinafter Referred to "cDNA"):

cDNA was synthesized using total RNA preparations (2 µg) in the presence of 1 µg oligo(dT)$_{12-18}$ and 400 U of reverse transcriptase Superscript II (Invitrogen) after digesting with 2 U DNase I (amplification grade, Invitrogen, USA) following the manufacturer's instructions.

Example-4

Amplification and Cloning of Cu/Zn SOD Gene:

Oligonucleotide primers listed in Table 1 were used to amplify PCR products from cDNA template. PCR was performed using 1 µl cDNA template, 0.2 µM each of left primer and right primer, 0.2 µM of dNTPs, 1 Unit of *Thermus aquaticus* (hereinafter, referred to "Taq") DNA polymerase (purchased from M/S. Qiagen, Germany), and 1×PCR buffer (20 mM Tris-HCl, pH 8.4, 50 mM KCl, 1.5 mM MgCl$_2$) in a final volume of 25 µl. Thermocycler program consisted of 35 cycles of initial denaturation at 94° C. for 3 min, followed by 94° C. for 30 sec, 55° C. for 45 sec and 72° C. for 1 min and then a final extension at 72° C. for 7 min. After the completion of PCR, 20 µl of PCR sample was run on 1.2% agarose gel in TAE buffer containing ethidium bromide (final concentration of 0.5 µg/ml). Amplicons were cut from the gel and DNA was eluted using QIAEX II gel extraction kit (M/S Qiagen, Germany), following the manufacturer's instructions. The purified DNA was cloned in pGEM-T easy vector (Promega, USA), Example-5

Sequencing and Analysis of Cloned cDNA:

The transformed bacterial cultures were randomly picked up using a pipette tip after streaking. The colony was suspended in 50 µl of lysis buffer [colony lysis buffer: TE (Tris-Cl 10 mM, 1 mM EDTA, pH 8.0) with 0.1% Tween 20)], boiled for 10 min in a water bath followed by snap cooling on ice. The cell debris was pelleted and supernatant (colony lysate) was collected. Plasmid released in the colony lysate was amplified using 0.2 µM of each 'forward' (5'-GTTG-TAAAACGACGGCCAGT-3') (SEQ ID NO:28) and 'reverse' (5'-CACAGGAAA CAGCTATGACC-3') (SEQ ID NO:29) flanking primers, 10 µM of dNTPs and 1 U of Taq DNA polymerase in 1×PCR buffer [20 mM Tris-Cl (pH, 8.4), 50 mM KCl, 1.5 mM MgCl$_2$]. In the present invention, dNTPs, a generic term, refers to the four deoxyribonucleotides: deoxyadenosine triphosphate (hereinafter, referred to "dATP"), deoxyguanosine triphosphate (hereinafter, referred to "dGTP"), deoxycytidine triphosphate (hereinafter, referred to "dCTP") and deoxythymidine triphosphate (hereinafter, referred to "dTTP"). Thermocycler program consisted of 30 cycles of 94° C. for 40 sec, 52° C. for 1 min and 72° C. for 2 min. This was followed by a 7 min extension at 72° C. Amplified products were run on 1.2% agarose gel in 1× TAE buffer (TAE buffer: 0.04 M Tris-acetate, 0.002 M EDTA, pH 8.5) containing ethidium bromide (working concentration of 0.5 µg/ml) and analyzed for correct size of insert by comparing with standard DNA molecular weight marker. Plasmids were isolated using the GenElute™ Plasmid Miniprep Kit (Sigma) following the manufacturer's instructions. These were quantified, checked on 1% agarose gel and sequenced using the BigDye terminator (version 3.1) cycle sequencing mix (Applied Biosystems, USA) on automated DNA sequencer (ABI Prism 310, Genetic Analyzer, Applied Biosystems, USA). Protocols were followed essentially as described by respective manufacturers. Sequencing primers used were 'forward' 5'-GTTGTAAAACGACGGCCAGT-3' (SEQ ID NO:28) and 'reverse' 5'-CAGGAAACAGCTAT-GACC-3' (SEQ ID NO:30).

Sequences mentioned in example 5 were searched for homology in the gene databases available at URL www.ncbi.nlm.nih.gov. Using Basic Local Alignment Search Tool (hereinafter, referred to "BLAST"). It was clear from the results that the sequences had homologies between 80-90% with the Cu/Zn SOD sequences available in the databases.

Example-6

Amplification and Cloning of Cu/Zn SOD Gene from Other Plant Species:

The primer sets listed in Table 1 have been used to amplify PCR products from cDNA templates from other plant species (*Camellia sinensis, Caragana jubata, Arnebia euchroma, Rheum emodi, Picrorhiza kurrooa, Stevia rebaudiana, Curcuma aromatica, Eragrostis atrovirens, Echinocloa crussgalia, Eleucine indica, Cynodon dactylone, Pennisetum clandistinum, Toona sinensis* and *Lantana camara*). Amplicons were cut from the gel and the respective DNA was eluted from the gel using QIAEX II gel extraction kit (from M/S Qiagen, Germany) following the manufacturer's instructions. The purified DNA was cloned in pGEM-T easy vector (Promega, USA), plasmids were isolated using the GenElute™ Plasmid Miniprep Kit (Sigma) following the manufacturer's instructions and sequenced using the BigDye terminator (version 3.1) cycle sequencing mix (Applied Biosystems, USA) on automated DNA sequencer (ABI Prism 310, Genetic Analyzer, Applied Biosystems, USA). The cloned products were analyzed using BLAST.

Example-7

Cloning of Amplified Partial Cu/Zn SOD in Expression Vector.

Partial Cu/Zn SOD sequences amplified from *Potentilla atrosanguinea*, *Curcuma aromatica* and *Lantana camara* were cloned into Isopropyl β-D-1-thiogalactopyranoside (hereinafter, referred to "IPTG") inducible pQE-30 UA expression vector (The QIAexpressionist, Qiagen) and transformed into competent *E. coli* cells. The plasmids were isolated using Genelute™ HP Plasmid Miniprep Kit (Sigma) and sequencing was performed using BigDye terminator (version 3.1) cycle sequencing mix (Applied Biosystems, USA) on an automated DNA sequencer (ABI Prism 3130, x1 Genetic Analyzer, Applied Biosystems) to confirm in frame cloning of the insert. Protocols were followed essentially as described by the manufacturer.

Example-8

Induction and Purification of Expressed Proteins:

*E. coli* cells containing partial Cu/Zn SOD genes from *Potentilla atrosanguinea*, *Curcuma aromatica* and *Lantana camara* were grown at 37° C. inside shaker incubator at 250 rpm in 50 ml of LB medium each, containing 100 µg ml$^{-1}$ and 25 µg ml$^{-1}$ kanamycin as antibiotics. IPTG was added to a final concentration of 1 mM, when cultures had grown to an absorbance of 0.6 at 600 nm to induce expression of the proteins. CuSO$_4$ and ZnSO$_4$ were added to a final concentration of 100 ppm and 2 ppm, respectively. After 5 h of protein induction at 37° C., cells were harvested by centrifugation at 4,000 ref at 4° C. for 20 min. Pellet was resuspended in 5 ml of lysis buffer (50 mM NaH$_2$PO$_4$ buffer, pH 8.0, containing 300 mM NaCl and 10 mM imidazole) and lysozyme was added to a final concentration of 1 mg/ml. Samples were incubated on ice for 30 minutes. The cell suspensions were sonicated, and the lysate obtained were cleared by centrifugation at 12000 g and 4° C. for 20 min. The supernatant from each fraction was loaded onto nickel-nitrilotriacitic acid (Ni-NTA) columns (Qiagen), washed with wash buffer (50 mM NaH$_2$PO$_4$ buffer, pH 8.0, containing 300 mM NaCl and 20 mM imidazole), and induced protein was eluted with elution buffer (50 mM NaH$_2$PO$_4$ buffer, pH 8.0, containing 300 mM NaCl and 250 mM imidazole). The different protein fractions obtained were analyzed by 15% SDS-PAGE using coomassie staining to visualize the protein (FIG. 2).

Example-9

In Silico Analysis of Cloned Cu/Zn SOD Sequences for Metal Binding Sites:

The amplified cDNA sequences from *Potentilla atrosanguinea* (SEQ ID NO:1), *Curcuma aromatica* (SEQ ID NO:9), and *Lantana camara* (SEQ ID NO:16) were translated and multiple aligned using GCG Wisconsin software tools. The aligned sequences were searched for copper/zinc binding domains. It is clear from the multiple alignments of deduced amino acid sequences that all the three cloned partial Cu/Zn SODs contained all the amino acid residues required for SOD activity. Copper binding residues included H45, H47, H62, and H119 whereas H62, H70, H79 and D82 involved in zinc binding when searched in corresponding position on full length cDNA cloned from *Potentilla atrosanguinea* (sequence has been reported in U.S. patent application Ser. No. 12/315,301).

Example-10

Localization of SOD by Activity Staining of Native Gel:

The SOD was localized on native-PAGE (12%) by activity staining as described by Beauchamp and Fridovich (Anal. Biochem. 1971; 44: 246-287). After electrophoresis, the gel was rinsed with 50 mM Potassium phosphate buffer (pH 7.8) for 10 minutes followed by 30 min incubation in 100 ml phosphate buffer (50 mM; pH 7.8) containing 2.5 mM NBT in dark at room temperature. Gel was then immersed in 1.17× 10$^{-6}$ M riboflavin for 20 min, followed by exposure to white light source (Nikon). Light exposure led to photogeneration of O$_2^-$., which converts NBT into insoluble purple colored formazan. Throughout the gel the purple color was developed except for the location where SOD was localized. Results obtained are depicted in FIGS. 3 and 6.

Example-11

Assaying the Partially Cloned Cu/Zn SOD cDNA Fragment(s) Encoded Proteins for SOD Activity:

In order to find whether the partially cloned Cu/Zn SOD cDNA fragments encode the catalytically active protein(s), the purified protein fractions assayed for SOD activity and autoclave stability. Protein fractions were divided into two fractions and transferred to two screw capped vials. One vial containing the enzyme was autoclaved (hereinafter, referred to heating at 121° C., at 1.1 kg per square cm for 20 min). For assaying SOD activity reaction medium contained 0.05 M potassium phosphate buffer (pH, 7.8), 5.7×10$^{-5}$ M nitroblue tetrazolium (hereinafter referred to NBT), 9.9×10$^{-3}$ M methionine, 1.17×10$^{-6}$ M riboflavin and 0.025% Triton X-100 in a total 3.0 ml volume. Reaction (performed in a 3.0 ml glass vial) was initiated by illuminating the reaction with light intensity of 1000µ Einstein/m$^2$/second using a fiber optic light source (Nikon). The reaction was carried out at room temperature, terminated after 2 min and the absorbance was read at 560 nm. A control reaction was always performed wherein all the steps and components were exactly the same as described above except that protein sample was replaced with equal volume of buffer. SOD competes with NBT for O$_2^-$., hence presence of SOD inhibits the color development. Activity of SOD is expressed as per cent inhibition in colour development as compared to the control reaction (higher the inhibition, higher the SOD activity). One unit of SOD activity is defined as the amount of SOD in a sample solution causing 50% inhibition of reduction of NBT in two min.

For determination of protein contents Protein Assay Dye Reagent (Bio-Rad, USA) based method was used. Bovine serum albumin (hereinafter referred to "BSA") was used as standard. The expressed partial Cu/Zn SOD protein from *Potentilla atrosanguinea*, *Curcuma aromatica* and *Lantana camara* were found to be catalytically active and even retained activities after autoclaving as shown in Table 2.

TABLE 2

Activity in recombinant SODs expressed in *E. coli* and purified using Ni-NTA columns.

| Sample name | % SOD activity retained after autoclaving |
|---|---|
| *Potentilla atrosanguinea* (full length) | 77.24 |
| *Potentilla atrosanguinea* (SEQ ID NO. 17) | 47.29 |
| *Curcuma aromatica* (SEQ ID NO. 18) | 76.77 |
| *Lantana camara* (SEQ ID NO. 19) | 48.70 |

Example-12

Partial Sequence Information Assisted Full Length Cu/Zn SOD cDNAs Cloning:

The partial cDNA sequences (SEQ ID NO: 4 and SEQ ID NO: 5, SEQ ID NO: 9) were used to design two sets of primers. Primers were designed such that the amplified 5' and 3' ends overlap each other over a small stretch of nucleotides. Rapid amplification of cDNA ends (hereinafter, referred to "RACE") was used to isolate full length SOD gene from *Caragana jubata* and *Curcuma aromatica*. RACE amplifies DNA sequences from a messenger RNA template between a defined internal site and unknown sequences of either the 3' or 5' end [Frohman, M. A., Dush, M. K. and Martin, G. R. (1988) Proc. Natl. Acad. Sci. USA 85: 8998-9002; U.S. Pat. Nos. 5,962,271 and 5,962,272]. A set of gene specific primers were used to generate 5' and 3' ends of the Cu/Zn SOD gene separately from *Caragana jubata* and *Curcuma aromatica*. A gene specific primer 1 for 5' RACE (hereinafter, referred to "GSP1") for primary PCR and one nested gene specific primer 1 (hereinafter, referred to "NES1"), for secondary PCR were designed. For 3' RACE a gene specific primer 2 (hereinafter, referred to "GSP2") for primary PCR and one nested primer 2 (hereinafter, referred to "NES2") were designed. Primers were designed such that the amplified 5' and 3' ends overlap each other over a small stretch of nucleotides. The cDNA for 5'-RACE was synthesized using a modified lock-docking oligo (dT) primer and SMART H A oligo (dT) primer. The modified oligo (dT) primer, termed the 5'-RACE CDS Primer (5'-CDS) has two degenerate nucleotide positions at the 3' end. In separate reactions, 1 mg of total RNA was reverse transcribed to yield 5' and 3' RACE ready cDNA using an enzyme known as reverse transcriptase. For 5' cDNA synthesis, the reaction was carried out using 1 µM of 5'-CDS primer in a reaction mixture containing RNA and 1 µM SMART II oligo (dT) primer. The 3'-RACE cDNA was synthesized using a traditional reverse transcription procedure, but with a special oligo (dT) primer. This 3'-RACE CDS Primer A (3'-CDS) included the lock-docking nucleotide positions as in the 5'-CDS and had a portion of the smart sequence at its 5' end. Sterile $H_2O$ was added to a final volume of 5 µl for each reaction, mixed and centrifuged. The reaction mix was incubated at 70° C. for 2 min and cooled on ice for 2 min. First-strand buffer [50 mM Tris-Cl (pH 8.3), 75 mM KCl and 6 mM $MgCl_2$], 1 mM dNTPs, 2 mM DTT and reverse transcriptase were added to each reaction and incubated at 42° C. for 1.5 h in an air incubator. Diluted the first-strand reaction product with 100 µl of Tricine-EDTA buffer [10 mM Tricine-KOH (pH 8.5), 1.0 mM EDTA] and heated tubes at 72° C. for 7 min (Reverse transcription system was a component of SMART RACE cDNA amplification kit from BD Biosciences, USA).

Sequences of Primers Used for RACE were as Follows (Purchased from BD Biosciences, USA as a Part of RACE Kit):

| Primer | Primer Sequence |
|---|---|
| SMART II A Oligonucleotide: | 5'-AAGCAGTGGTATCAACGCAGAGTACGCGGG-3' (SEQ ID NO: 31) |
| 3'- RACE CDS Primer A (3'- CDS): | 5'-AAGCAGTGGTATCAACGCAGAGTAC(T)$_{30}$N$_{-1}$N-3' (SEQ ID NO: 32) |
| 5'- RACE CDS Primer (5'- CDS): | 5'-(T)$_{25}$ N$_{-1}$N-3' (SEQ ID NO: 33) |
| 10X Universal Primer Mix A (UPM): | Long: 5'-TAATACGACTCACTATAGGGCA AGCAGTGGTATCAACGCAGAGT-3' (SEQ ID NO: 34) Short: 5'-CTAATACGACTCACTATAGGGC-3' (SEQ ID NO: 35) |
| Nested Universal Primer A (NUP): | 5'-AAGCAGTGGTATCAACGCAGAGT-3' (SEQ ID NO: 36) |

Sequences of Gene Specific Primers Used for RACE to Amplify Cu/Zn SOD from *Caragana jubata*:

| Primer | Primer Sequence |
|---|---|
| GSP1: | 5'-TGGGCATGAACTTAGCAAAACTACCGG-3' (SEQ ID NO: 37) |
| NES1: | 5'-GTTGTTGTCCATGGTGATCCTGATGAT-3' (SEQ ID NO: 38) |
| GSP2: | 5'-TATCACTGTTGGGGATGACGGAACTGCT-3' (SEQ ID NO: 39) |
| NES2 | 5'-ATTGGTAGGGCTGTTGTTGTCCATGCAG-3' (SEQ ID NO: 40) |

Sequences of Gene Specific Primers Used for RACE to Amplify Cu/Zn SOD from *Curcuma aromatica*:

| Primer | Primer Sequence |
|---|---|
| GSP1: | 5'-CTGCATGGACAACAACAGCCCTACCAAT-3'. (SEQ ID NO: 41) |
| NES1: | 5'-GCTAGCGAGGATGGTATTGTTGCTGTC-3'. (SEQ ID NO: 42) |
| GSP2: | 5'-TATCACTGTTGGGGATGACGGAACTGCT-3'. (SEQ ID NO: 43) |
| NES2 | 5'-ATTGGTAGGGCTGTTGTTGTCCATGCAG-3'. (SEQ ID NO: 44) |

RACE cDNA (5' and 3') were amplified using 0.2 µM of GSP1, GSP2 and 1× universal primer (UPM), 0.2 mM dNTP and 1× BD polymerase mix. Thermocycler program consisted of 30 cycles of 94° C. for 30 sec, 68° C. for 30 sec and 72° C. for 3 min. The reaction was up-scaled to 50 µl and after the completion of PCR, 45 ηl of PCR sample was run on 1.2% agarose gel in 1× TAE buffer containing ethidium bromide (final concentration of 0.5 µg/ml) (FIG. 4). Rest of the amplified product was stored at −20° C. for secondary PCR, if needed. Amplicons were cut from the gel and DNA was eluted from the gel using QIAEX II gel extraction kit (from M/S Qiagen, Germany) following the manufacturer's instructions. The purified DNA was cloned in pGEM-T easy vector (Promega, USA), plasmids were isolated using the GenElute™ Plasmid Miniprep Kit (Sigma) following the manufacturer's instructions and sequenced using the BigDye terminator (version 3.1) cycle sequencing mix (Applied Biosystems, USA) on automated DNA sequencer (ABI Prism 3130, x1 Genetic Analyzer, Applied Biosystems, USA). The RACE products were analyzed by BLAST.

Example 13

Cloning of Amplified Sods in Expression Vector:

Full-length cDNAs of Cu/Zn SOD sequences amplified from *Caragana jubata* and *Curcuma aromatica* were cloned into Isopropyl β-D-1-thiogalactopyranoside (hereinafter, referred to "IPTG") inducible pQE-30 UA expression vector (The QIAexpressionist, Qiagen) and transformed into competent *E. coli* cells (M15 strain). The plasmids were isolated using Genelute™ HP Plasmid Miniprep Kit (Sigma) and sequencing was performed using BigDye terminator (version 3.1) cycle sequencing mix (Applied Biosystems, USA) on an automated DNA sequencer (ABI Prism 3130, x1 Genetic Analyzer, Applied Biosystems) to confirm in frame cloning of the insert. Protocols were followed essentially as described by the manufacturer.

Example-14

Induction and Purification of Expressed Proteins:

*E. coli* cells containing Cu/Zn SOD genes from *Caragana jubata* and *Curcuma aromatica* were grown at 37° C. inside shaker incubator at 250 rpm in 50 ml of LB medium each, containing 100 µg ml$^1$ and 25 ml$^{-1}$ kanamycin as antibiotics. IPTG was added to a final concentration of 1 mM, when cultures had grown to an absorbance of 0.6 at 600 nm to induce expression of the proteins. $CuSO_4$ and $ZnSO_4$ were added to a final concentration of 100 ppm and 2 ppm, respectively. After 5 h of protein induction at 37° C., cells were harvested by centrifugation at 4,000×g at 4° C. for 20 min. Pellet was resuspended in 5 ml of lysis buffer (50 mM $NaH_2PO_4$ buffer, pH 8.0, containing 300 mM NaCl and 10 mM imidazole) and lysozyme was added to a final concentration of 1 mg/ml. Sample was incubated on ice for 30 minutes. The cell suspension were sonicated, and the lysate obtained was cleared by centrifugation at 12,000×g and 4° C. for 20 min. Supernatant was loaded onto nickel-nitrilotriacitic acid (Ni-NTA) columns (Qiagen), washed with wash buffer (50 mM $NaH_2PO_4$ buffer, pH 8.0, containing 300 mM NaCl and 20 mM imidazole), and induced protein was eluted with elution buffer (50 mM $NaH_2PO_4$ buffer, pH 8.0, containing 300 mM NaCl and 250 mM imidazole). The different protein fractions obtained were analyzed by 15% SDS-PAGE using silver staining to visualize the protein (FIG. 5).

Example-15

Effect of Temperature on Expressed Proteins:

The stability of the enzyme as a function of temperature was determined by quantifying the residual activity before and after autoclaving (hereinafter, referred to heating at 121° C., at 1.1 kg per square cm for 20 min) at different assay temperatures ranging from −10° C. to +10° C. Recombinant proteins of *Potentilla atrosanguinea, Caragana jubata, Curcuma aromatica* were desalted against 50 mM potassium phosphate buffer using Small wonder lyser (Excellion Innovations and Inventions Inc, Pragati Biomedical) and divided into two fractions. Purified, desalted protein was transferred to two screw capped vials. One vial containing the enzyme was autoclaved. The unautoclaved and autoclaved recombinant Cu/Zn SODs were localized on native-PAGE (12%). Equal quantity in terms of volume was loaded of unautoclaved and autoclaved fractions (FIG. 6). Activity staining was performed as explained in example 10. For assaying SOD activity microtiter plate based micro-assay procedure was employed. All the reagents were prepared in potassium phosphate buffer (50 mM, pH-7.8). The SOD assay reaction mixture contained riboflavin ($1.17 \times 10^{-6}$ M), Triton X 100 (0.025%), Nitroblue tetrazolium (hereinafter, referred to "NBT") ($5.7 \times 10^{-5}$ M), methionine ($9.9 \times 10^{-3}$ M) and potassium phosphate buffer (50 mM, pH-7.8) in a total volume of 200 µl. A control reaction was performed in which potassium phosphate buffer (50 mM, pH-7.8) was added to the SOD assay reaction mixture instead of the SOD sample. SOD assay was performed at different temperatures using thermomixture (Eppendorf). In case of SOD assay at sub-zero temperatures 50% glycerol was added in the reaction mixture to avoid freezing at low temperature. The reaction was initiated by placing the reaction mix inside 0.5 ml plastic tubes containing enzyme. Individual control reactions were set up. Tubes were exposed with white light source for 10 min and subsequently reaction mix was transferred into microtitre palte. The absorbance was recorded at 560 nm wavelength using microplate reader (Synergy HT, with Gen5 controlling software, Bioteck, USA). Activity of SOD was expressed by inhibition in color development as compared to the control reaction. Higher the inhibition, higher would be the SOD activity. The protein fractions showing the SOD activity were used in further purification protocol. Protein content was determined as described in example 11. The expressed full length Cu/Zn SOD protein from *Potentilla atrosanguinea, Caragana jubata* and *Curcuma aromatica* were found to be catalytically active and even retained activities after autoclaving as shown in Table 3.

татable 3 showing effect of temperature on SOD activity of recombinant *Potentilla atrosanguinea*, *Curcuma aromatica* and *Caragana jubata* Cu/Zn SODs.

| Assay Temperature | % SOD activity retained after autoclaving Source of SOD gene | | |
|---|---|---|---|
| (° C.) | Potentilla | Caragana | Curcuma |
| −10.0 | 60.42 | 42.58 | 19.9 |
| 0.0 | 95.26 | 78.29 | 56.84 |
| 4.0 | 86.10 | 46.91 | 54.69 |
| 10.0 | 77.34 | 85.13 | 62.51 |

Example-16 pH Optima of Expressed Proteins:

In order to determine pH optima of expressed recombinant proteins, separate reaction mix for carrying out SOD assay were prepared by using different buffers of pH values: 0.05 M Glycine-HCl (pH 3.0), 0.05 M Acetate buffer (pH 4.0, 5.0), Potassium phosphate buffer (pH 6.0, 7.0, 8.0), or 0.05 Carbonate—bicarbonate buffer (pH 9.0, 10.0). Microtitre plate based SOD assay were carried out in triplicates for recombinant *Potentilla atrosanguinea*, Caragana jubata and Curcuma aromatica Cu/Zn SOD proteins. Separate controls were kept for each pH value. pH optima of individual recombinant proteins is plotted in FIG. 7.

The Main Advantages of the Present Invention are:
1. Oligonucleotide primer sets have been designed from the selected regions so that the cloned fragments include the Cu/Zn binding domains which are necessary for the SOD activity.
2. Oligonucleotide primer sets have been designed from the selected regions so that these can also pick up the variabilities if present in Cu/Zn SOD genes.
3. These oligonucleotide primers have been used for the amplification of Cu/Zn SOD gene from diverse plant species.
4. The partial sequences of Cu/Zn SOD amplified using these primers can be used for cloning of full length Cu/Zn SOD gene.
5. Full length cDNA encoding SOD from Caragana jubata has been cloned.
6. Full length cDNA encoding SOD from Curcuma aromatica has been cloned.
7. Full length cDNA of SOD from Caragana jubata has been expressed in prokaryotic expression vector.
8. Full length cDNA of SOD from Curcuma aromatica has been expressed in prokaryotic expression vector.
9. The recombinant SOD-protein encoded by SOD gene from Caragana jubata has been found to be autoclave stable.
10. The recombinant SOD-protein encoded by SOD gene from Curcuma aromatica has been found to be autoclave stable.

We claim:

1. A degenerate primer set comprising at least as primers two polynculeotides comprising SEQ ID NOs:24 and 25 or SEQ ID NOs:26 and 27, wherein the primer set is adapted to amplify stress tolerant superoxide dismutase (SOD) from plant species.

2. The primer set of claim 1, wherein the primers comprise four polynucleotides comprising SEQ ID Nos:24 to 27.

3. The primer set of claim 1 comprising at least as primers polynucleotides comprising SEQ ID NOs:24 and 25, wherein the primers comprising SEQ ID NOs:24 and 25 are further defined as:
   being 21 nucleotides long;
   having a G+C content in the range of about 38% to about 62%;
   having a Tm in the range of about 49° C. to about 58° C.;
   having an annealing temperature that is in the range of about 53° C. to about 58° C.; and
   having an optimal annealing temperature for SOD detection that is about 55° C.

4. The primer set of claim 1 comprising at least as primers polynucleotides comprising SEQ ID NOs:26 and 27, wherein the primers comprising SEQ ID NOs:26 and 27 are further defined as:
   being 21 nucleotides long;
   having a G+C content in the range of about 33% to about 62%;
   having a Tm in the range of about 47° C. to about 56° C.;
   having an annealing temperature that is in the range of about 52° C. to about 58° C.; and
   having an optimal annealing temperature for SOD detection that is about 55° C.

5. A method of amplifying stress tolerant SOD comprising:
   amplifying SOD with the primer set of claim 1, wherein the primers comprise two polynucleotides comprising SEQ ID NOs:24 and 25; and
   obtaining a gene product that is about 390 base pairs long.

6. A method of amplifying stress tolerant SOD comprising:
   amplifying SOD with the primer set of claim 1, wherein the primers comprise two polynucleotides comprising SEQ ID NOs:26 and 27; and
   obtaining a gene product that is about 280 base pairs long.

7. A method of obtaining stable stress tolerant superoxide dismutase (SOD) from plant species comprising:
   isolating the total RNA from leaf tissue;
   synthesizing complementary DNA from the isolated RNA;
   obtaining primers for amplifying the Cu/Zn SOD gene, wherein each primer comprises a nucleotide sequence selected from the group consisting of SEQ ID NOs:24 to 27;
   and amplifying the Cu/Zn SOD gene using the obtained primers to provide an amplified product.

8. The method of claim 7, wherein the plant species is selected from the group consisting of *Camellia sinensis*, *Caragana jubata*, *Arnebia euchroma*, *Rheum emodi*, *Picrorhiza kurrooa*, *Stevia rebaudiana*, *Curcuma aromatica*, *Eragrostis atrovirens*, *Echinocloa crussgalia*, *Eleucine indica*, *Cynodon dactylone*, *Pennisetum clandistinum*, *Toona sinesis* and *Lantana camara*.

9. The method of claim 8, wherein the Cu/Zn SOD gene is shorter than the full-length Cu/Zn SOD gene from the plant species.

10. The method of claim 9, wherein the Cu/Zn SOD gene comprises a nucleotide sequence selected from the group consisting of SEQ ID NOs:1 to 16.

11. The method of claim 8, wherein the Cu/Zn SOD gene is a full-length Cu/Zn SOD cDNA.

12. The method of claim 11, wherein the full-length Cu/Zn SOD cDNA comprises a nucleotide sequence selected from the group consisting of SEQ ID NOs:20 to 23.

13. The method of claim 7, wherein the amplifying is by polymerase chain reaction (PCR).

14. The method of claim 13, wherein the PCR comprises:
   incubating a sample comprising the synthesized complementary DNA and obtained primers at 94° C. for 3 min;
   performing 35 amplification cycles, wherein each cycle comprises incubating the sample and incubating the sample at 72° C. for 7 min.

15. The method of claim 7, further comprising:
   ligating the amplified product into a vector to provide a recombinant plasmid;
   transforming the recombinant plasmid into a cell; and
   purifying the stable stress tolerant superoxide dismutase from the transformed cells.

16. The method of claim 15, wherein the purified stable stress tolerant superoxide dismutase is further defined as having enzymatic activity under one or more stress parameters selected from the group consisting of high temperature, high pressure, and sub-zero temperature.

17. The method of claim 16, wherein the purified stable stress tolerant superoxide dismutase is further defined as having enzymatic activity at high temperature, and the high temperature is further defined as in the range of about 100° C. to about 121° C.

18. The method of claim 16, wherein the purified stable stress tolerant superoxide dismutase is further defined as having enzymatic activity at high pressure, and the high pressure is further defined as in the range of about 14 pounds per square inch (psi) to about 15 psi.

19. The method of claim 16, wherein the purified stable stress tolerant superoxide dismutase is further defined as having enzymatic activity at sub-zero temperature, and the sub-zero temperature is further defined as in the range of about 0° C. to about minus 10° C.

20. The method of claim 7, further comprising detecting expression of Cu/Zn SOD genes in an organism using the amplified Cu/Zn SOD product.

21. The method of claim 20, wherein the organism is a plant, animal, or microbe.

22. The method of claim 7, further comprising expressing the amplified product in a plant to provide a stress tolerant transgenic plant.

23. The method of claim 7, wherein the amplified product comprises a nucleotide sequence selected from the group consisting of SEQ ID NOs:1 to 23.

24. The method of claim 23, further comprising using the amplified product to amplify an upstream promoter region of the Cu/Zn SOD gene.

25. The method of claim 23, further comprising using the amplified product to identify and clone one or more intron regions of the Cu/Zn SOD gene.

26. The method of claim 23, further comprising using the amplified product to synthesize SOD proteins.

27. The method of claim 23, further comprising:
providing the amplified product to an animal; and
obtaining antibodies produced by the animal against the amplified product.

28. The method of claim 27, wherein the animal is a rabbit or goat.

29. A kit for PCR-based detection and identification of stress tolerant superoxide dismutase in diverse plant species comprising the degenerate primer set of claim 1.

* * * * *